US011109929B2

(12) United States Patent
Nakanishi

(10) Patent No.: US 11,109,929 B2
(45) Date of Patent: Sep. 7, 2021

(54) MEDICAL TOOL GRIP MECHANISM WHICH GRIPS AND CONTROLS MEDICAL TOOL

(71) Applicant: MEDICAROID CORPORATION, Kobe (JP)

(72) Inventor: Tetsuya Nakanishi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 734 days.

(21) Appl. No.: 15/659,903

(22) Filed: Jul. 26, 2017

(65) Prior Publication Data

US 2018/0036089 A1 Feb. 8, 2018

(30) Foreign Application Priority Data

Aug. 5, 2016 (JP) .............................. JP2016-154581

(51) Int. Cl.
*A61B 34/00* (2016.01)
*A61B 34/37* (2016.01)
*B25J 15/00* (2006.01)
*A61B 17/00* (2006.01)
*A61B 34/30* (2016.01)

(52) U.S. Cl.
CPC .............. *A61B 34/74* (2016.02); *A61B 34/37* (2016.02); *B25J 15/00* (2013.01); *A61B 2017/00477* (2013.01); *A61B 2034/305* (2016.02); *A61B 2034/742* (2016.02)

(58) Field of Classification Search
CPC ... A61B 34/74; A61B 34/37; A61B 2034/742; A61B 2017/00477; B25J 15/00
See application file for complete search history.

(56) References Cited

U.S. PATENT DOCUMENTS

| 4,674,501 | A | | 6/1987 | Greenberg |
| 5,201,325 | A | * | 4/1993 | McEwen ................ A61B 17/02 600/202 |
| 5,618,303 | A | | 4/1997 | Marlow et al. |
| 5,649,956 | A | * | 7/1997 | Jensen ................... B25J 9/1065 403/316 |
| 5,807,378 | A | * | 9/1998 | Jensen ....................... B25J 3/04 606/1 |

(Continued)

FOREIGN PATENT DOCUMENTS

| JP | H07-031623 A | 2/1995 |
| JP | 2002-537884 A | 11/2002 |

(Continued)

*Primary Examiner* — Shirley X Jian
(74) *Attorney, Agent, or Firm* — Metrolex IP Law Group, PLLC

(57) ABSTRACT

One or more embodiments provide medical tool grip mechanism to which multiple types of medical instruments can be attached. A grip mechanism grips an instrument. The instrument has a shaft extending in a longitudinal direction, a treatment tool arranged at a distal end of the shaft, and a treatment tool control portion that is arranged at a proximal end of the shaft and controls the treatment tool. The grip mechanism has a gripping portion. The gripping portion grips the treatment tool control portion such that the treatment tool control portion is rotatable about a rotational axis extending in the longitudinal direction of the shaft, and movable in the longitudinal direction with respect to the shaft.

19 Claims, 22 Drawing Sheets

(56) References Cited

U.S. PATENT DOCUMENTS

| | | |
|---|---|---|
| 6,436,107 B1 | 8/2002 | Wang et al. |
| 7,524,320 B2 | 4/2009 | Tierney et al. |
| 2012/0041478 A1 | 2/2012 | Jaspers |
| 2013/0310813 A1 | 11/2013 | Kaercher et al. |
| 2014/0107690 A1 | 4/2014 | Ishii et al. |
| 2014/0236147 A1* | 8/2014 | Schneider .............. A61B 17/29 606/41 |

FOREIGN PATENT DOCUMENTS

| | | |
|---|---|---|
| JP | 2005-522262 A | 7/2005 |
| WO | 2012160715 A1 | 11/2012 |

* cited by examiner

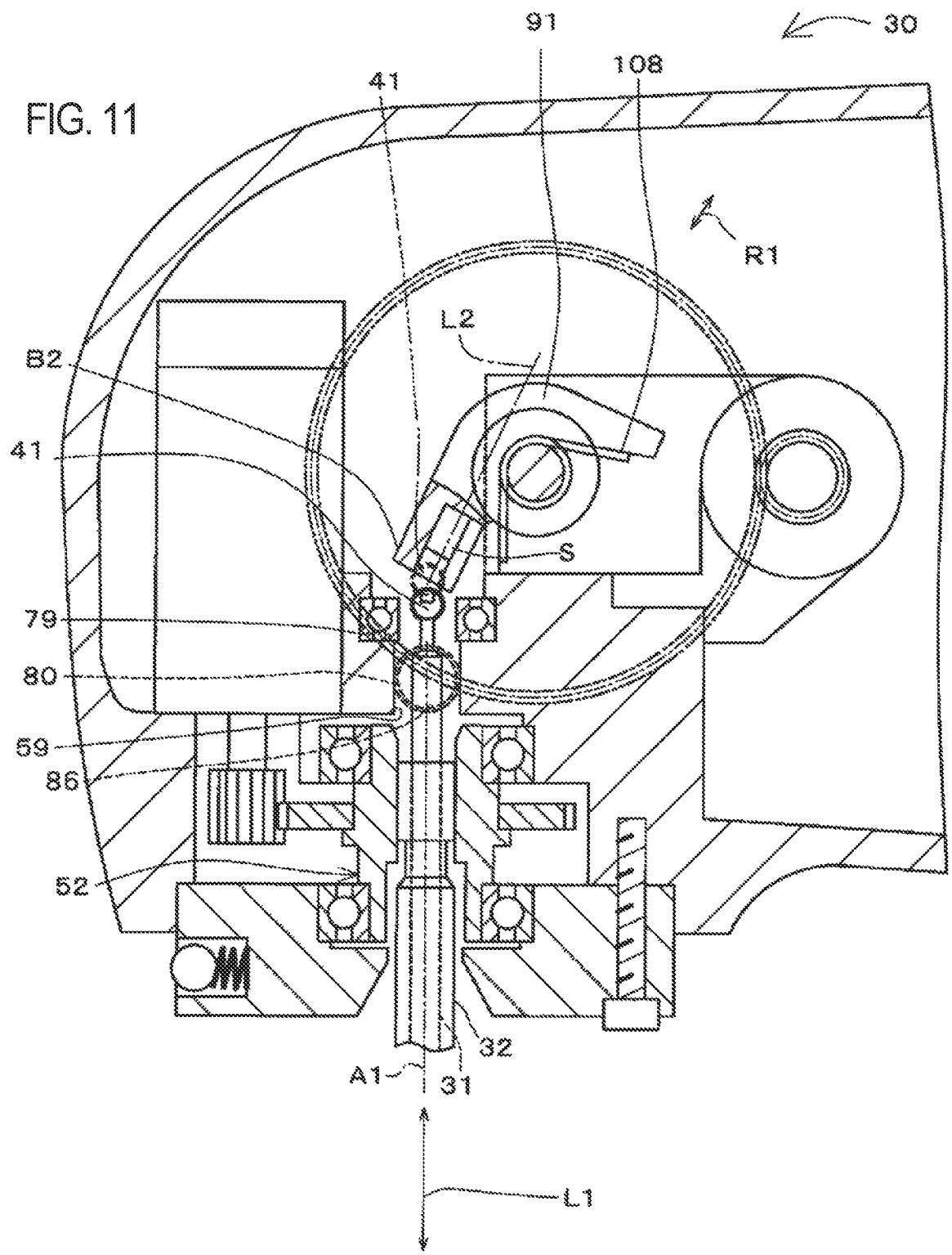

MEDICAL TOOL GRIP MECHANISM WHICH GRIPS AND CONTROLS MEDICAL TOOL

CROSS-REFERENCE TO RELATED APPLICATION

This application claims priority to Japanese Patent Application No. 2016-154581 filed on Aug. 5, 2016, the entire disclosure of which is incorporated by reference herein.

TECHNICAL FIELD

One or more embodiments disclosed herein relate to a medical tool grip mechanism which grips a medical tool, such as forceps, and operates the medical tool.

BACKGROUND ART

Systems including a robotic manipulator arm for use in a surgical operation have been known (see, e.g., U.S. Pat. No. 7,524,320).

Robotic manipulators of surgery assisting robot systems, such as those disclosed in U.S. Pat. No. 7,524,320, hold one end portion of a tool, such as forceps, and moves this tool toward a treatment target (i.e., a patient) which is a human being or an animal to assist an operator in performing surgery on the treatment target.

SUMMARY

Conventional surgery assisting robots are configured to use a dedicated medical tool applicable to its manipulator arm, and are not able to use general medical instruments. Thus, forceps manufacturers or other instrument manufactures need to provide dedicated products applicable only to a specific surgery assisting robot, which is a disadvantage.

In view of the above background, an object of one or more embodiments disclosed herein is to provide a medical tool grip mechanism to which multiple types of medical instruments can be attached.

To achieve the above object, a medical tool grip mechanism according to one or more embodiments grips a medical tool having a shaft extending in a longitudinal direction, a treatment tool arranged at one end portion of the shaft, and a treatment tool control portion which is arranged at the other end portion of the shaft and controls the treatment tool. The medical tool grip mechanism includes a gripping portion configured to grip the treatment tool control portion such that the treatment tool control portion is rotatable about an axis extending in the longitudinal direction of the shaft and is movable in the longitudinal direction with respect to the shaft.

This configuration allows a robot to grip a medical tool in such a manner that allows a treatment tool to be rotated and opened/closed, even if the medical tool is a general tool used, for example, in surgery performed by a human, and allows the operator to remote control the medical tool.

BRIEF DESCRIPTION OF THE DRAWINGS

FIG. 11 is a diagram illustrating a cross-sectional view of the grip mechanism from which the instrument is detached, as viewed from the side.

DETAILED DESCRIPTION

[First Example Configuration]
[General Description of Surgical Operation System]

Figure 1:
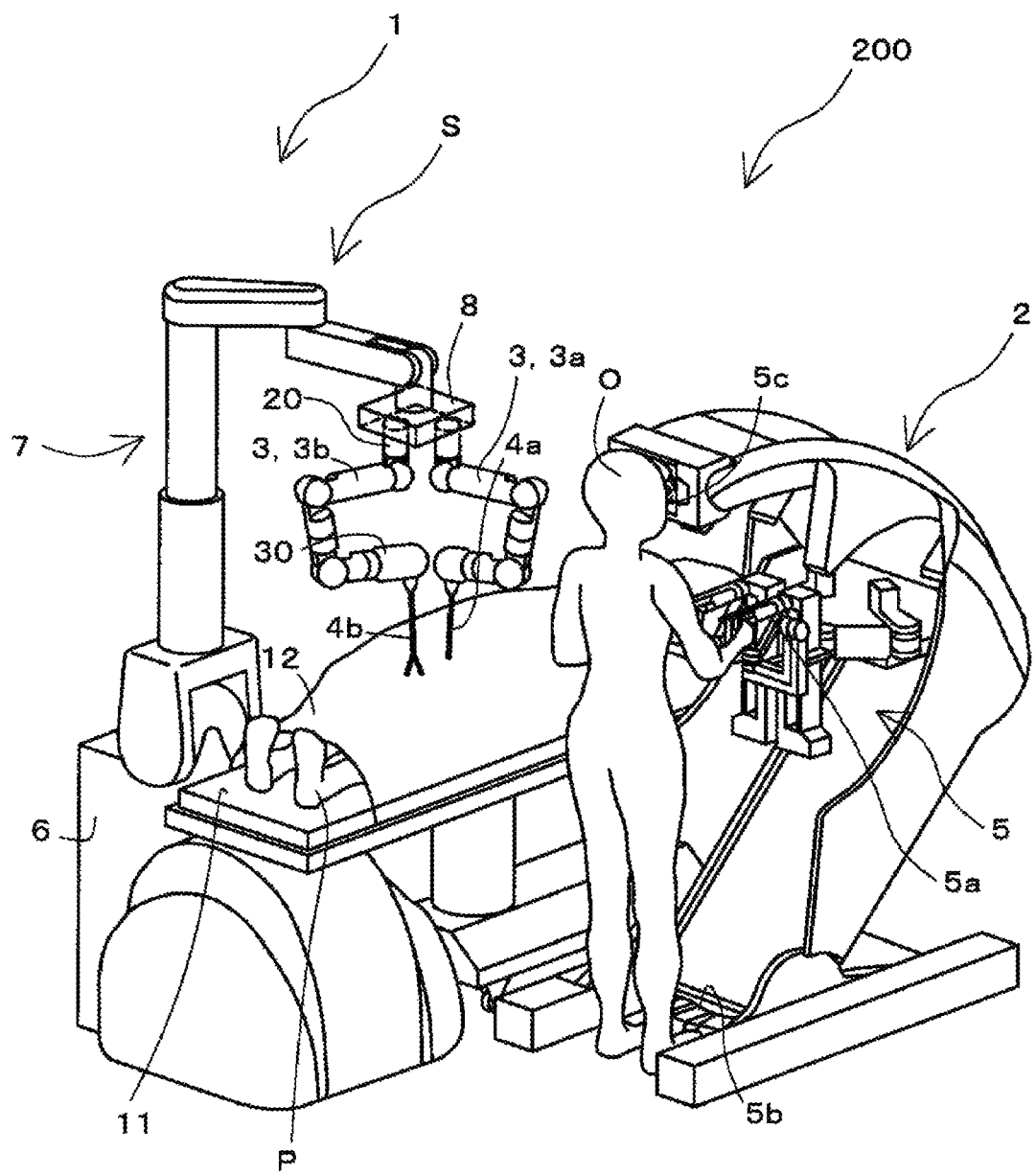
FIG. 1 is a diagram schematically illustrating a general configuration of a surgical operation system according to a first example configuration of one or more embodiments.

FIG. 1 is a diagram schematically illustrating a general configuration of a surgical operation system 200 according to a first example configuration of one or more embodiments. As illustrated in FIG. 1, the surgical operation system 200 allows an operator O (e.g., a doctor) to perform an endoscope surgical operation on a treatment target P (e.g., a human being or an animal), using a patient-side system 1, as in a robot-assisted surgery, a remote robotic surgery, etc.

The surgical operation system 200 has the patient-side system 1 and an operating apparatus 2 which operates the patient-side system 1. The operator O inputs, to the operating apparatus 2, a movement instruction instructing the patient-side system 1 to make the movement instructed. The operating apparatus 2 transmits this movement instruction to the patient-side system 1. The patient-side system 1 receives the movement instruction transmitted from the operating apparatus 2, and moves an endoscope assembly 4a, an instrument (i.e., a medical tool) 4b, etc., included in the patient-side system 1, based on the movement instruction. Elements of the surgical operation system 200 will be described in detail below.

[Example Configuration of Operating Apparatus]

The operating apparatus 2 serves as an interface between the surgical operation system 200 and the operator O, and remote-controls the patient-side system 1. The operating apparatus 2 includes an operation input section 5 which includes a manipulator arm 5a, an operation pedal 5b, etc., which are operated by the operator O to input the movement instruction, and a monitor 5c which displays an image taken by the endoscope assembly 4a. The operator O operates the operation input section 5 to input the movement instruction to the operating apparatus 2, while viewing the target site on the monitor 5c. The movement instruction input to the operating apparatus 2 is transmitted to a controller 6, which will be described later, of the patient-side system 1 by cable or radio.

[Example Configuration of Patient-Side System]

The patient-side system 1 includes: a positioner 7; a platform 8 attached to an end of the positioner 7; a plurality of patient-side manipulator arms (hereinafter simply referred to as "arms 3") detachably attached to the platform 8; the endoscope assembly 4a attached to an end of an arm 3a, which is one of the plurality of arms 3; the instrument 4b detachably attached to an end of an arm 3b, which is the rest of the plurality of arms 3 besides the arm 3a; and the controller 6 which controls the movement of the patient-side system 1.

In the patient-side system 1, elements (from the positioner 7 to a grip mechanism 30 gripping the instrument 4b) are serially connected to each other. In this specification, an end of each of the series of elements which is on the side closer to a contact portion of the positioner 7 with the floor of the operating room is called a "proximal end" and the opposite end is called a "distal end."

The instrument 4b for use as a medical tool is supported on a medical tool grip mechanism 30 arranged at a distal end of the arm 3b, in such a manner that the instrument 4b is attachable to, and detachable from, the medical tool grip mechanism 30. The medical tool grip mechanism 30 may also be simply referred to as a grip mechanism 30.

An end effector having a movable joint is used as the instrument 4b, i.e., a medical tool. Examples of the end effector include scissors, grasping forceps (or a grasper), a needle holder, a monopolar hook, a monopolar spatula, a bipolar instrument, a micro dissector, a stapler, a tucker, a suction cleaning tool, a knife, and a clip applier. An endoscope may also be used as the medical tool. An embodiment in which the instrument 4b is grasping forceps (or a grasper) will be described below as an example.

In the patient-side system 1 configured as described above, the controller 6 which has received a movement instruction from the operating apparatus 2 moves the positioner 7 and positions the platform 8 first so that the platform 8 and a surgical table 11, or the platform 8 and a treatment target P, have a predetermined positional relationship.

Then, the controller 6 positions the arms 3a, 3b such that the endoscope assembly 4a and the instrument 4b have predetermined initial positional relationships with cannulas (not shown) retained on the body surface of the treatment target P. The controller 6 moves the arms 3a, 3b to provide appropriate displacement, as well as changes in postures, of the endoscope assembly 4a and the instrument 4b, in response to the movement instruction transmitted from the operating apparatus 2, while, in principle, keeping the positioner 7 still. Surgery is performed by the respective instruments 4b making such a movement.

Figure 2:
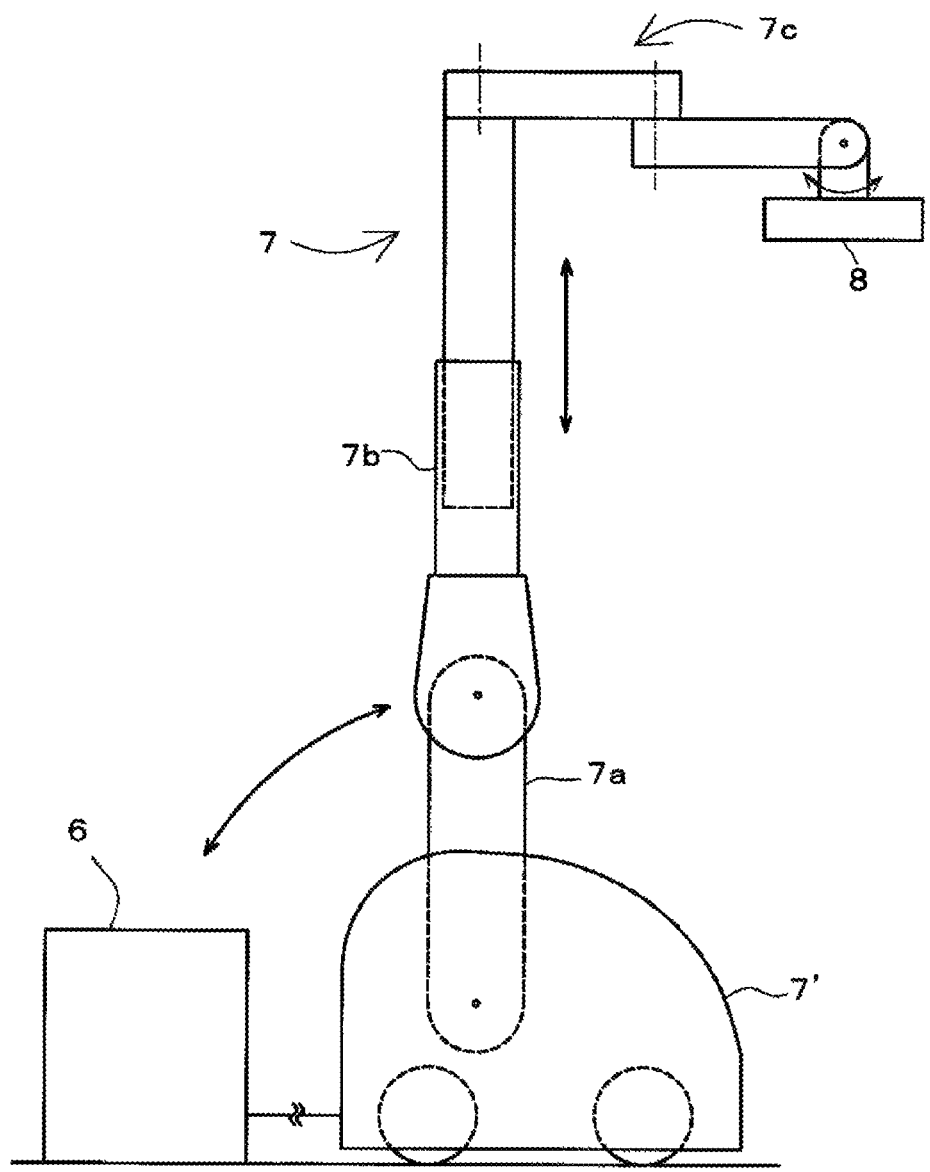
FIG. 2 is a diagram illustrating a side view of a general configuration of a positioner.

FIG. 2 is a diagram illustrating a side view of a general configuration of the positioner 7. As illustrated in FIG. 2, the positioner 7 has a basic structure of a horizontal articulated robot, and includes a base 7' placed on the floor of an operating room, an up-and-down shaft 7b, a swinging arm 7a which couples the base 7' and a proximal end of the up-and-down shaft 7b, and a horizontal arm 7c coupled to a distal end of the up-and-down shaft 7b. The platform 8 is coupled to a distal end of the horizontal arm 7c.

At least one of the position and the posture of the arm 3a, 3b coupled to the platform 8 is changed by a swing movement of the swinging arm 7a, an up-and-down movement of the distal end of the up-and-down shaft 7b, a horizontal movement of the distal end of the horizontal arm 7c, and a swing movement of the platform 8 with respect to the distal end of the horizontal arm 7c.

Figure 3:
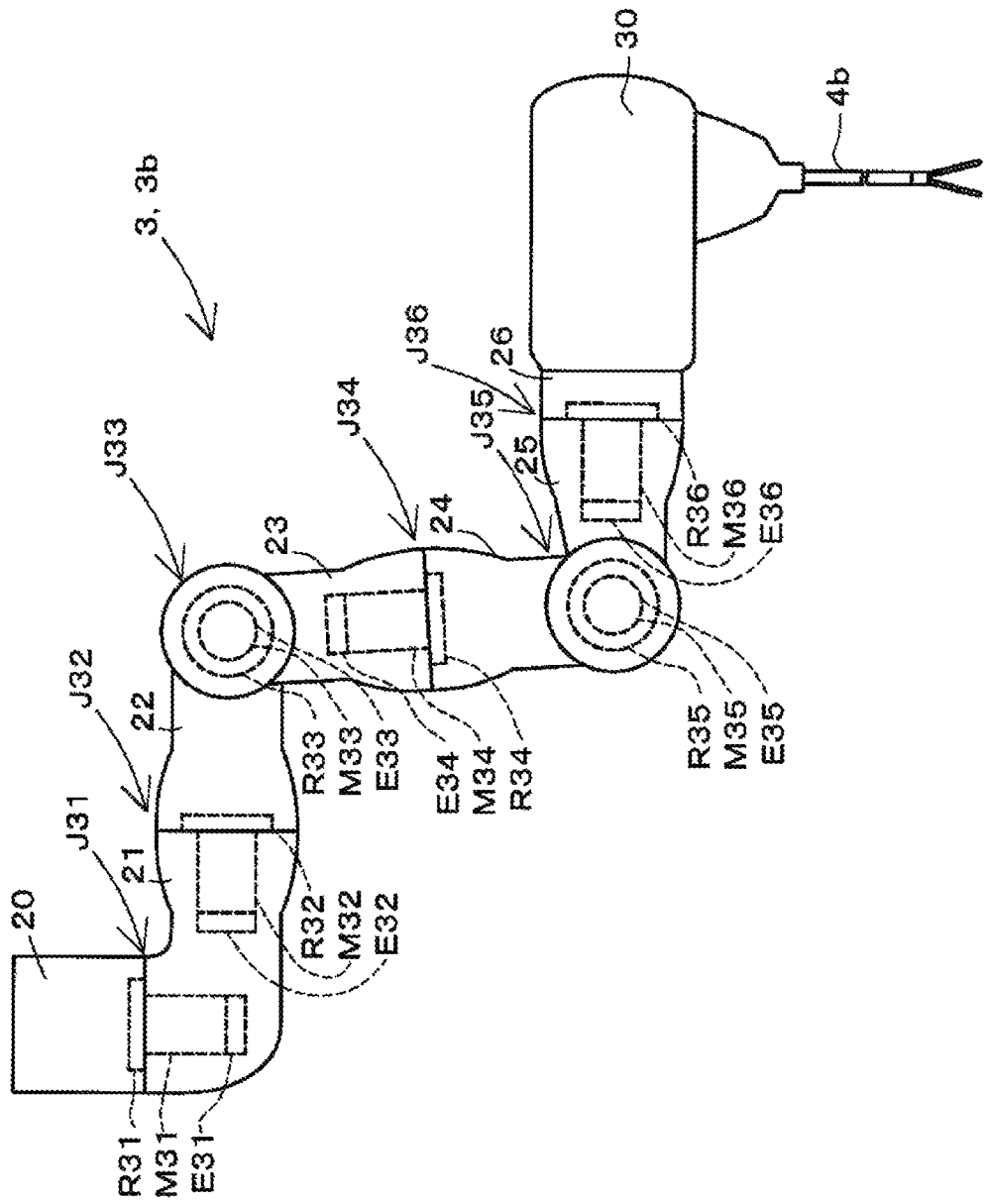
FIG. 3 is a diagram illustrating a side view of schematic configurations of an arm and an instrument included in a patient-side system.

FIG. 3 is a diagram illustrating a schematic configuration of the arm 3 (i.e., the arm 3b) included in the patient-side system 1. As illustrated in FIGS. 1 and 3, each of the arms 3 is configured such that its distal end is movable with respect to its proximal end in a three-dimensional space. Since the arms 3a, 3b have similar configurations, the arm 3b will be described in this example configuration.

The arm 3 includes a base 20 detachably attached to the platform 8, and first to sixth links 21-26 connected sequentially from the base 20 toward the distal end of the arm 3. More specifically, a proximal end of the first link 21 is coupled to a distal end of the base 20 via a twisting joint J31. A proximal end of the second link 22 is coupled to a distal end of the first link 21 via a twisting joint J32. A proximal end of the third link 23 is coupled to a distal end of the second link 22 via a bending joint J33. A proximal end of the fourth link 24 is coupled to a distal end of the third link 23 via a twisting joint J34. A proximal end of the fifth link 25 is coupled to a distal end of the fourth link 24 via a bending joint J35. A proximal end of the sixth link 26 is coupled to a distal end of the fifth link 25 via a twisting joint J36. A proximal end of the instrument 4b is coupled to a distal end of the sixth link 26.

The arm 3 configured as described above is equipped with driving servomotors M31-M36, encoders E31-E36 which detect rotational angles of the servomotors M31-M36, and speed reducers R31-R36 which reduce the speed of outputs of the servomotors M31-M36 and increase the torque. These elements correspond to the joints J31-J36, respectively.

In this configuration, the controller 6 servo-controls the servomotors M31-M36 such that the distal end of the arm 3 reaches the position, and achieves the posture, which correspond to an instruction regarding the position and posture, based on the movement instruction input to the operating apparatus 2 and the rotational angle detected by the encoders E31-E36.

As described earlier, the grip mechanism 30 is attached to the sixth link 26, which is located at the distal end of the arm 3. The grip mechanism 30 is configured to be displaced by the displacement of the sixth link 26 of the arm 3. The instrument 4b is attachable to, and detachable from, the grip mechanism 30.

[Example Configuration of Instrument as Medical Tool]

Figure 4:
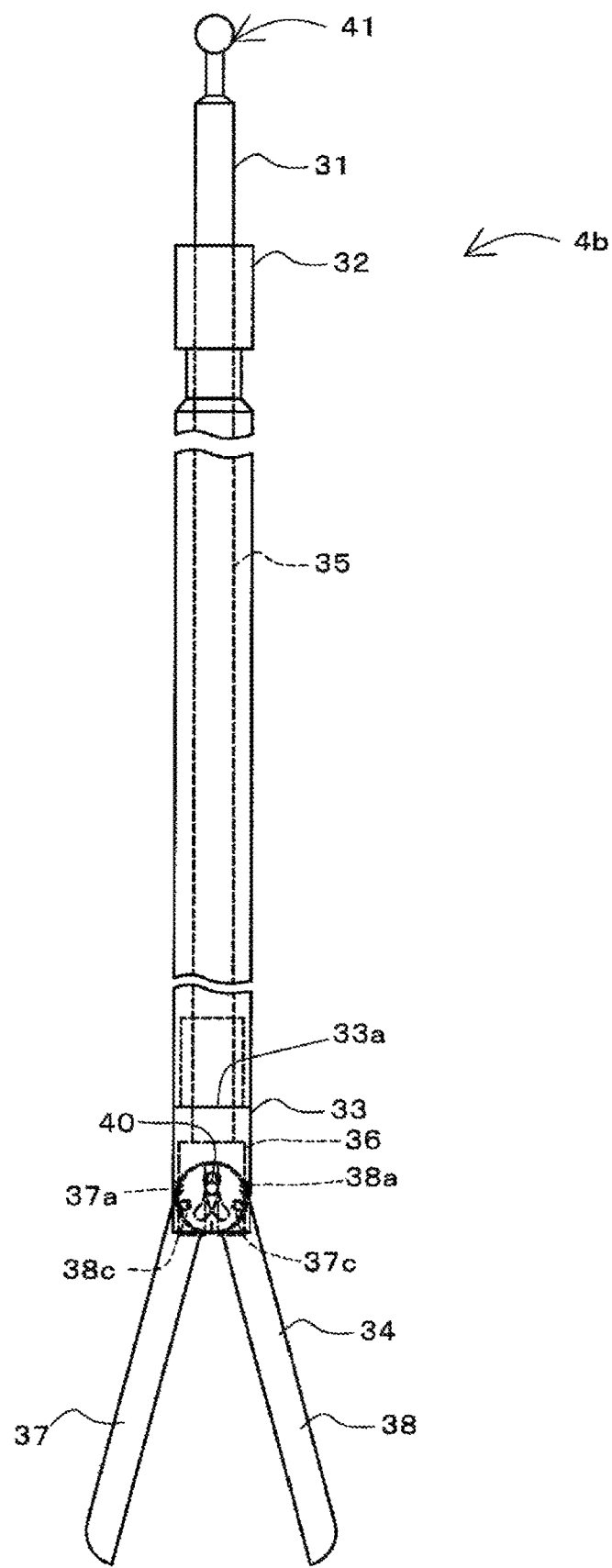
FIG. 4 is a diagram illustrating a side view of an example instrument.
Figure 5:
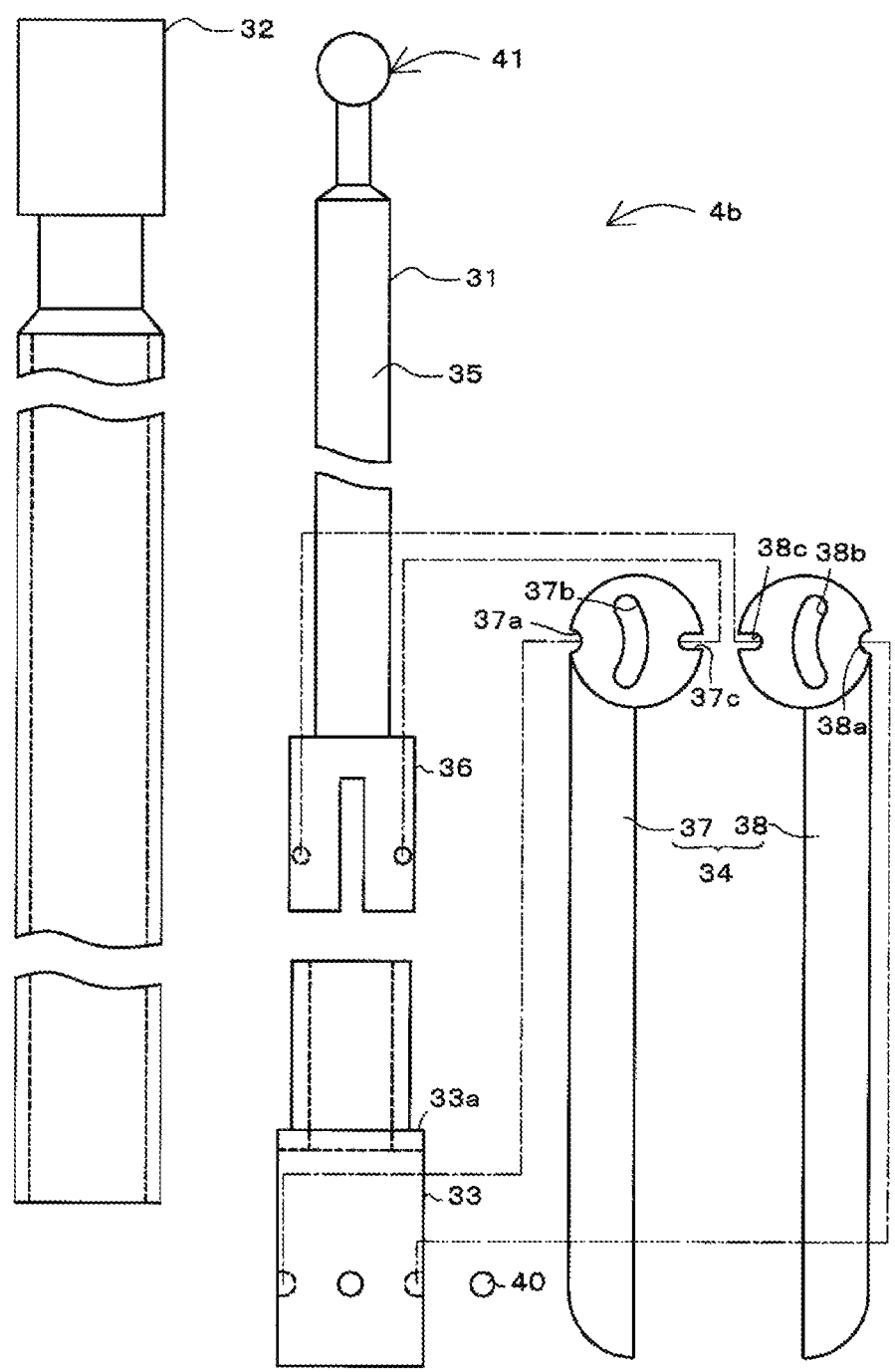
FIG. 5 is an exploded diagram of the instrument.

FIG. 4 is a diagram illustrating a side view of an example of the instrument 4b. FIG. 5 is an exploded diagram of the instrument 4b. In FIGS. 4 and 5, part of the instrument 4b is not shown. In this example configuration, the instrument 4b is grasping forceps (or a grasper) and is used to hold a tissue of the body of the treatment target P. The instrument 4b may also be monopolar or bipolar forceps to which electric power is fed from an energy device.

The instrument 4b is comprised of an insert 31, a shaft 32, an insert end portion 33, and a treatment tool 34. When used, the insert 31 and the shaft 32 are coupled to each other, with the insert 31 being inserted in the shaft 32.

The portions 31, 32, 33, 34 of the instrument 4b are made of synthetic resin, metal, or other materials. The portions 31, 32, 33, 34 of the instrument 4b are positioned close to the tissues of the body of the treatment target P. Thus, preferably, the portions are each made of a biocompatible material.

The shaft 32 serves as a shell which covers a large portion of the instrument 4b, and has a cylindrical shape extending straight along a longitudinal direction L1. In general, the shaft 32 has a diameter of 5 mm or 10 mm. The shaft 32 includes a cylindrical shaft body which forms a large part of the shaft 32, and a half plate having a cylindrical shape, including portions with different diameters, and fixed to a proximal end of the shaft body.

The insert end portion 33 has a cylindrical shape, and is configured to hold the treatment tool 34 and a moving element (which is a rod 35 of the insert 31 in this example configuration) such that the treatment tool 34 and the moving element are movable in conjunction with each other. A portion of the insert end portion 33 closer to the proximal end thereof is provided with an annular step 33a. The distal end of the shaft body 32a of the shaft 32 is seated on this step 33a, and is fixed to the proximal end of the insert end portion 33 by fitting or screwing.

The insert 31 includes the rod 35 as a moving element, a linkage portion 36 arranged on a distal end side of the rod 35, and a treatment tool control portion 41 arranged on a proximal end of the rod 35.

The rod 35, which serves as a moving element of the insert 31, is a member which transmits a movement of the treatment tool control portion 41 at the proximal end of the insert 31 to the treatment tool 34, and moves the treatment tool 34. The rod 35 passes through the shaft 32 in a state in which the insert 31 is coupled to the shaft 32. The rod 35 is displaceable with respect to the shaft 32 in the longitudinal direction L1.

The linkage portion 36 is a plate-like portion located in the insert end portion 33, and is coupled to the treatment tool 34.

The treatment tool 34 includes a pair of elongate jaws 37, 38 in this example configuration. The jaw 37 is provided, at its proximal end, with a fulcrum point portion 37a coupled to a bearing portion provided at the insert end portion 33, an arc-shaped hole 37b, and a load point portion 37c coupled to a drive shaft provided at the linkage portion 36. The arc-shaped hole 37b forms an arc shape whose center of curvature is the fulcrum point portion 37a. A pin 40 which passes through the insert end portion 33 passes through the arc-shaped hole 37b. This configuration prevents the jaw 37 from being detached from the insert end portion 33. The displacement of the insert 31 (the linkage portion 36) in the longitudinal direction L1 causes the jaw 37 to swing about the fulcrum point portion 37a.

The jaw 38 has a configuration similar to that of the jaw 37, and moves in conjunction with the jaw 37. The jaw 38 is provided, at its proximal end, with a fulcrum point portion 38a coupled to the bearing portion provided at the insert end portion 33, an arc-shaped hole 38b, and a load point portion 38c coupled to the drive shaft provided at the linkage portion 36. The arc-shaped hole 38b forms an arc shape whose center of curvature is the fulcrum point portion 38a. The pin 40 which passes through the insert end portion 33 passes through the arc-shaped hole 38b. This configuration prevents the jaw 38 from being detached from the insert end portion 33. The displacement of the insert 31 (the linkage portion 36) in the longitudinal direction L1 causes the jaw 38 including the load point portion 38c to swing about the fulcrum point portion 38a. In this configuration, the displacement of the insert 31 with respect to the shaft 32 in the longitudinal direction L1 causes the tips of the jaws 37, 38 to displace in a direction toward each other and in a direction away from each other. The treatment tool 34 is opened and closed in this manner.

The treatment tool control portion 41 is provided to control the treatment tool 34 by utilizing a force received from outside the treatment tool 4b. The treatment tool control portion 41 has a spherical shape in this example configuration. In this example configuration, the treatment tool control portion 41 is gripped by a gripping portion 91 (see FIG. 6), which will be described later, of the grip mechanism 30.

In the above configuration, the shaft 32 is attachable to, and detachable from, the insert 31. In assembly of the instrument 4b, the rod 35 of the insert 31 is inserted in the shaft 32 so as to pass through the shaft 32. When the insert 31 is inserted in the shaft 32 to a point where the shaft 32 is seated on the step 33a of the insert end portion 33, the shaft 32 is fixed to the insert end portion 33 by fitting or screwing.

[Example Configuration of Grip Mechanism]

Figure 6:
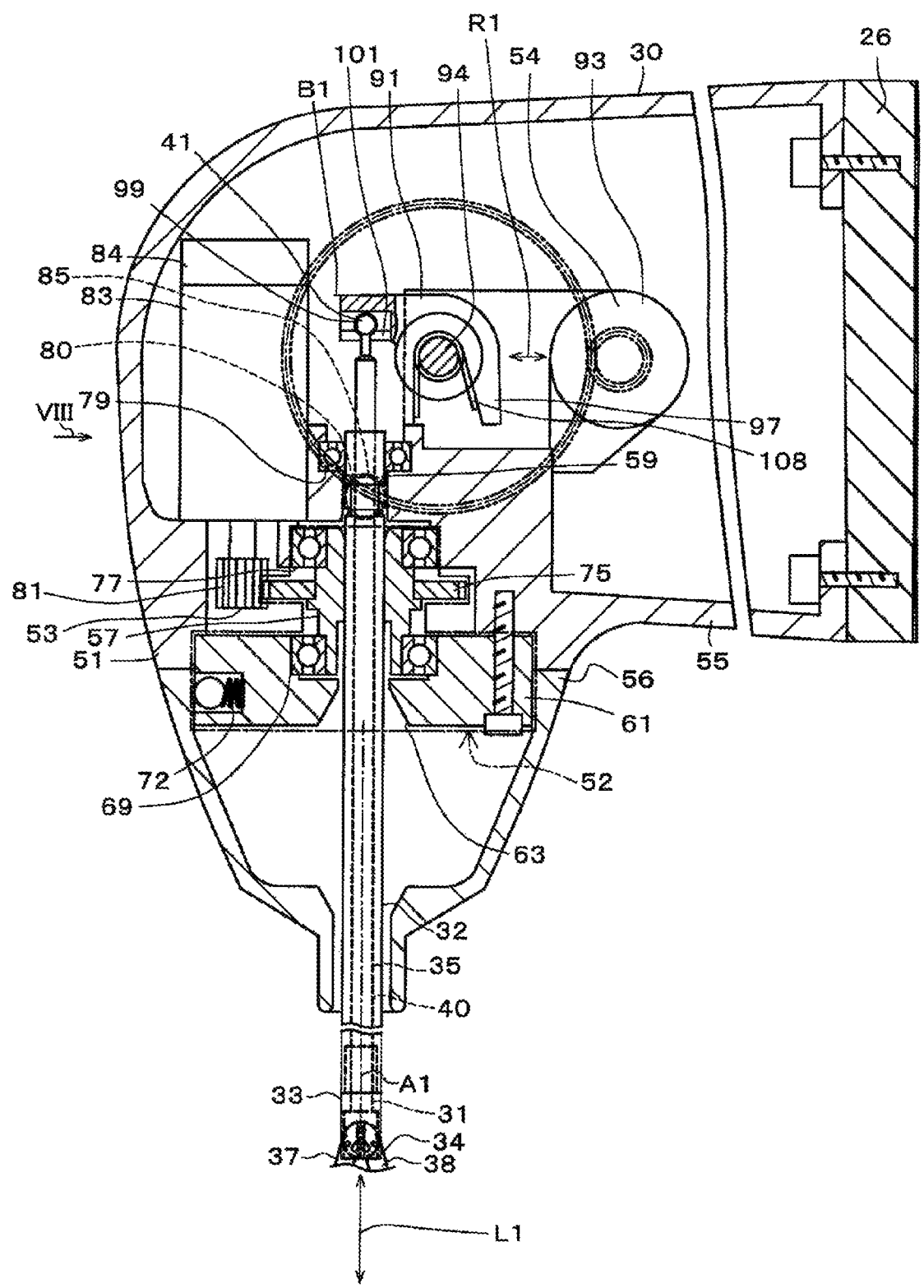
FIG. 6 is a diagram illustrating a cross-sectional view of a grip mechanism, as viewed from the side.
Figure 7:
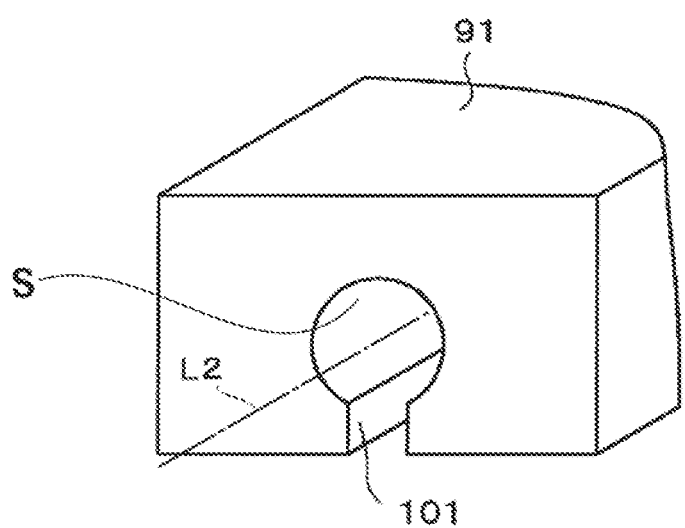
FIG. 7 is a diagram illustrating a perspective view of a main part of a gripping portion of the grip mechanism.
Figure 8:
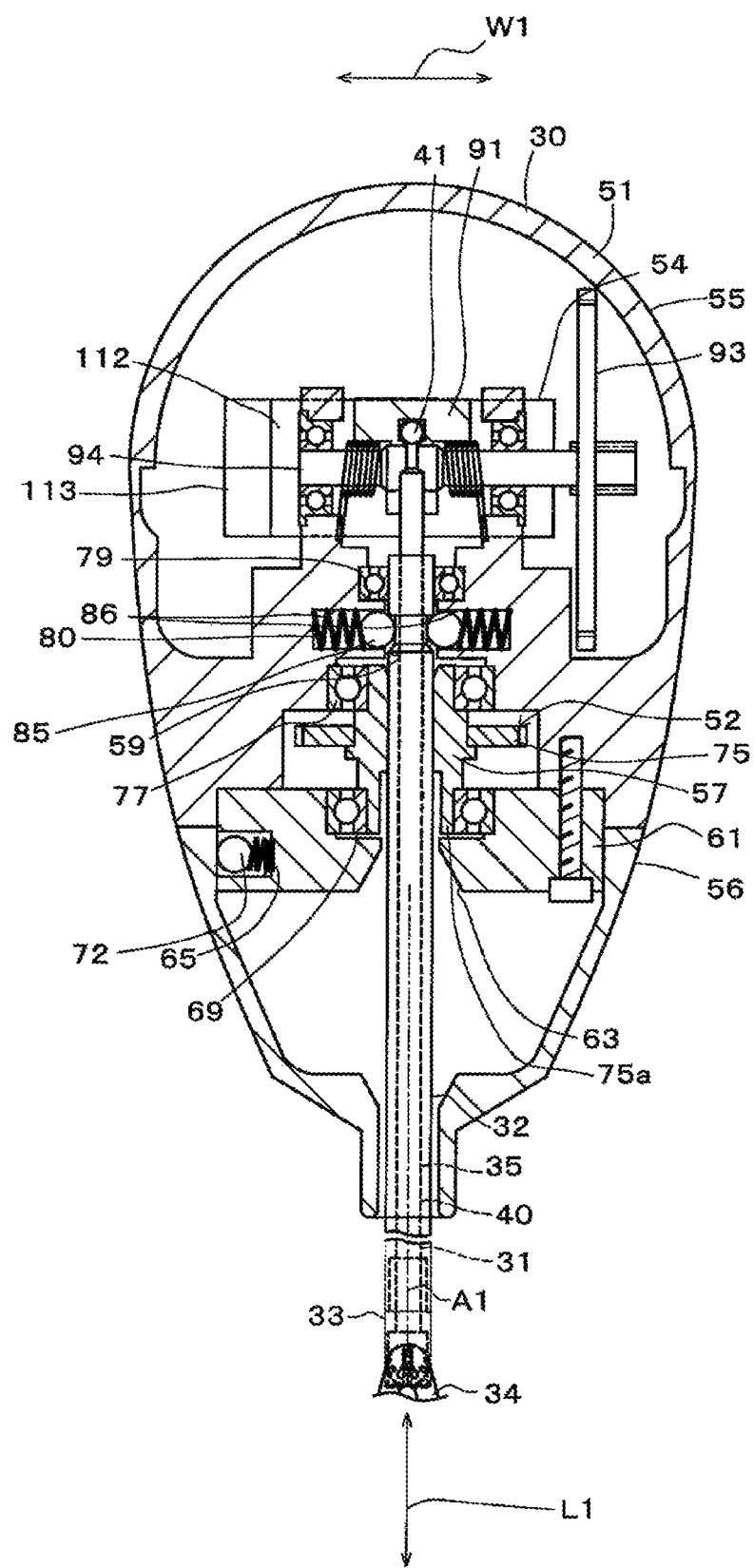
FIG. 8 is a diagram illustrating a cross-sectional view of the grip mechanism, as viewed from the front (i.e., in a direction of the arrow VIII in FIG. 6).
Figure 9:
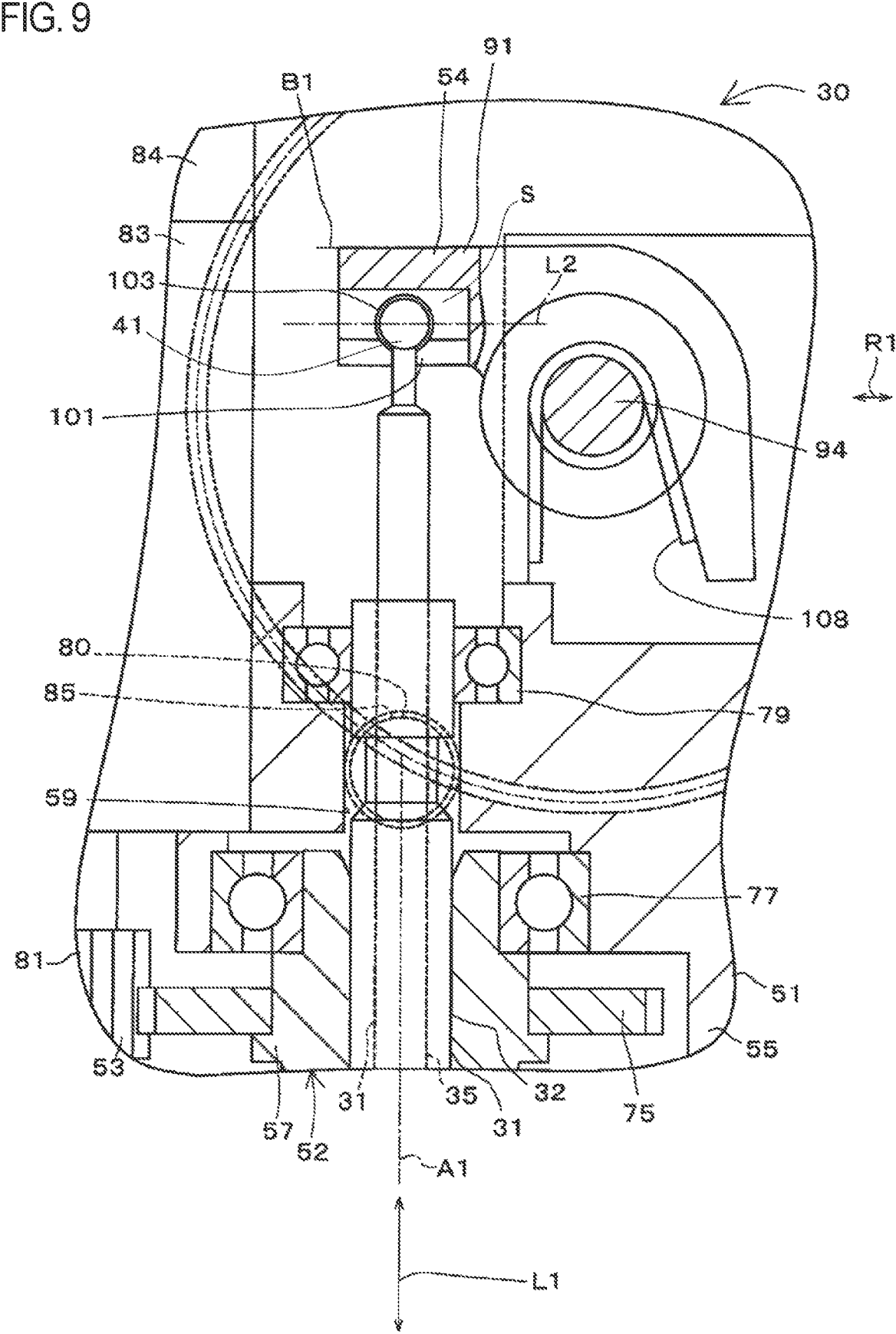
FIG. 9 is a diagram illustrating an enlarged view of a main part of the grip mechanism of FIG. 6.
Figure 10:
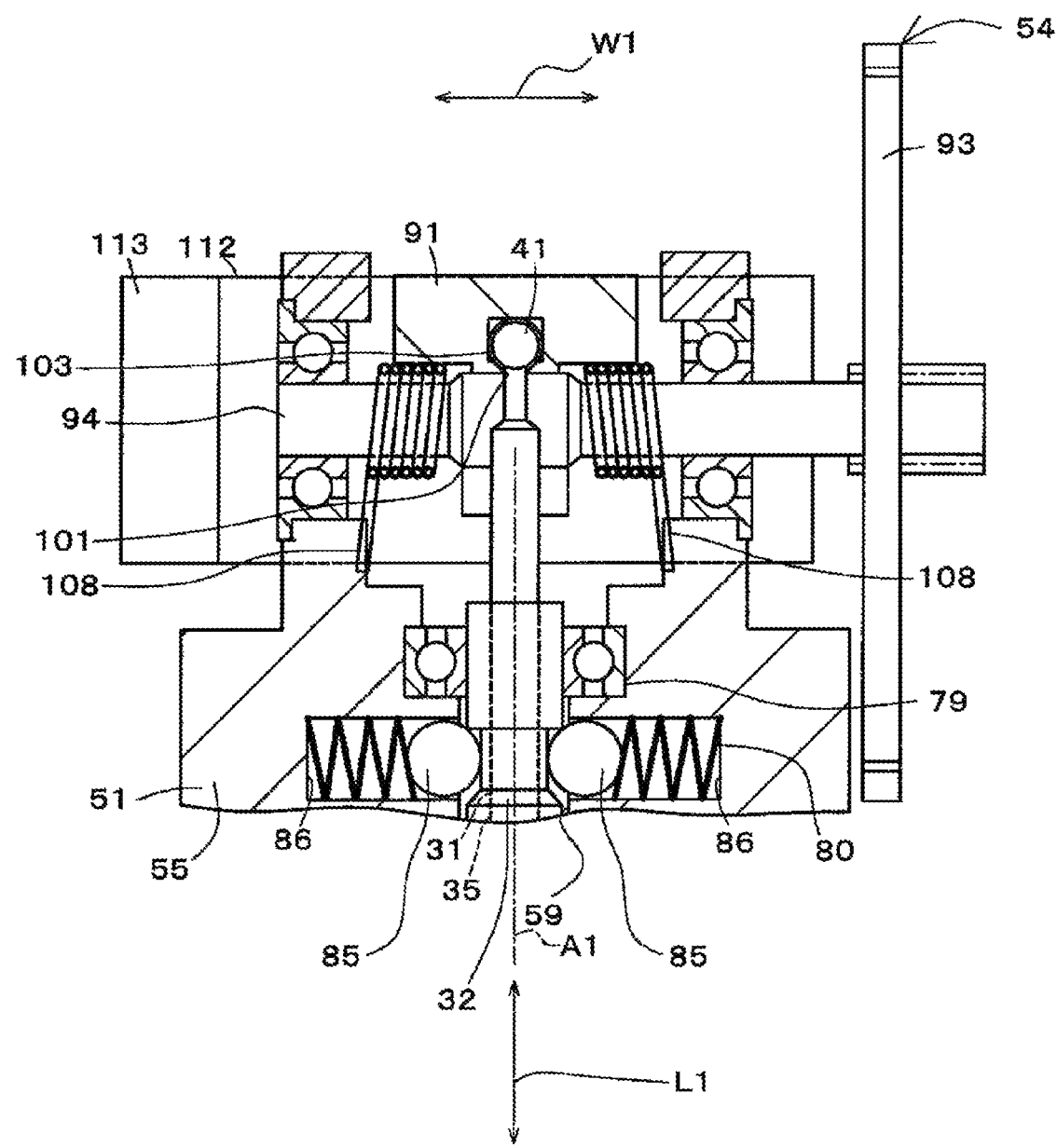
FIG. 10 is a diagram illustrating an enlarged view of a main part of the grip mechanism of FIG. 8.

FIG. 6 is a diagram illustrating a cross-sectional view of the grip mechanism 30, as viewed from the side. FIG. 7 is a diagram illustrating a perspective view of a main part of the gripping portion 91 of the grip mechanism 30. FIG. 8 is a diagram illustrating a cross-sectional view of the grip mechanism 30, as viewed from the front (i.e., in a direction of the arrow VIII in FIG. 6). FIG. 9 is a diagram illustrating an enlarged view of a main part of the grip mechanism 30 of FIG. 6. FIG. 10 is a diagram illustrating an enlarged view of a main part of the grip mechanism 30 of FIG. 8. FIG. 11 is a diagram illustrating a cross-sectional view of the grip mechanism 30 from which the instrument 4b is detached, as viewed from the side.

The grip mechanism 30 extends from the sixth link 26 of the arm 3 along the longitudinal direction of the sixth link 26. The dimension of the grip mechanism 30 in a direction orthogonal to the longitudinal direction is smaller than the dimension thereof in the longitudinal direction. This configuration contributes to a reduction in the moment of inertia of the grip mechanism 30, allowing the arm 3 to be actuated and controlled by a smaller actuator.

The grip mechanism 30 includes a tool support unit 52, a tool rotating mechanism 53, an operation mechanism 54, and a housing 51 accommodating these elements.

The housing 51 includes a housing body 55 and a cover 56 which is attachable to, and detachable from, the housing body 55.

The housing body 55 has a through hole 59 in which the instrument 4b is inserted.

The cover 56 is detached from, and attached to, the housing body 55 for replacement of the instrument 4b, inner cleaning of the grip mechanism 30, maintenance of the grip mechanism 30, etc.

The cover 56 is in a funnel-like shape as a whole, and has a portion gradually tapered toward the distal end.

The cover 56 has a hollow which forms a space capable of housing the instrument 4b. The cover 56 has a distal end portion, the inner circumferential surface of which forms a cylindrical shape whose diameter is greater than the diameter of the shaft 32 of the instrument 4b, so that the cover 56 is prevented from coming into contact with the instrument 4b with a small gap left therebetween. This configuration reduces the entry of foreign substances into the cover 56.

The tool support unit 52 includes a tool support 57, a gear 75, bearings 69, 77, and an inner cover 61.

The inner cover 61 is provided with a hole 63. The hole 63 is chamfered such that the diameter thereof is reduced toward the proximal end. In the present embodiment, the hole 63 is located at approximately the center of the inner cover 61. This configuration serves as a guide for the instrument 4b. The instrument 4b is thus inserted smoothly.

The inner cover 61 houses a ball plunger 72 as a pressing mechanism. The ball plunger 72 includes an elastic member, such as a coil spring or rubber, and a ball pressed radially outward of the inner cover 61 by the elastic member. The inner circumferential surface of the opening of the cover 56 is pressed by a pressing mechanism, such as the ball plunger 72, and is therefore pressed by the outer circumferential surface of the inner cover 61. As a result, the cover 56 is frictionally engaged with the inner cover 61. The pressing mechanism is not limited to the ball plunger. The pressing mechanism may have only the elastic member, such as a coil spring or rubber, or have any other structures.

The tool support 57 is provided to support the instrument 4b rotatably about a rotational axis A1 extending in the longitudinal direction L1 of the shaft 32. Driving force is input to the tool support 57 from a first actuator 83, which will be described later.

The tool support 57 has a cylindrical shape, and supports the shaft 32 by pressing the shaft 32. The tool support 57 and the shaft 32 are rotatably coupled to each other by frictional engagement.

Further, how the tool support 57 and the shaft 32 are coupled to each other is not limited to a specific configuration as long as the shaft 32 is detachable from the tool support 57, and as long as the tool support 57 and the shaft 32 are rotatable in an integrated manner.

The tool rotating mechanism 53 includes a driving section 81 coupled to the gear 75 in a power transmittable manner, the first actuator 83 which gives driving force to the driving section 81, and a first encoder 84.

The first actuator 83 is an electric motor in this example configuration, but is not limited to a specific configuration as long as the first actuator 83 is capable of rotatably driving the tool support 57.

The first encoder 84 is a position detector, and is attached to the first actuator 83. The encoder as the position detector may be replaced with a resolver or a potentiometer. The driving section 81 and the gear 75 function as a speed reducer mechanism which slows down the speed of the output rotation of the output shaft of the first actuator 83, thereby amplifying the torque. A gear-type speed reducer mechanism is used as the speed reducer mechanism in this example configuration. However, other speed reducer mechanisms may also be provided, such as a pulley-type speed reducer mechanism in which the gear is replaced with a plurality of pulleys connected via a belt.

A retaining mechanism 80 supports the shaft 32 of the instrument 4b rotatably about the rotational axis A1, and is configured to be decoupled from the shaft 32 when a force greater than or equal to a specific value acts between the retaining mechanism 80 and the shaft 32 in the longitudinal direction L1.

In this example configuration, the retaining mechanism 80 is a pair of ball plungers 85, 85, which are housed in housing holes 86, 86 formed in the housing body 55 and extending in a direction orthogonal to the longitudinal direction L1 from the through hole 59. Each ball plunger 85 includes an elastic member, such as a coil spring or rubber, and a ball pressed radially inward of the through hole 59 by the elastic member.

Points of the pair of ball plungers 85, 85 which come in contact with the shaft 32 can be adjusted in the radial direction of the shaft 32 according to the diameter of the shaft 32 of the instrument 4b. It is therefore possible to attach instruments 4b in different types and diameters. The retaining mechanism 80 is not limited to the ball plunger 85. The retaining mechanism 80 may have only the elastic member, such as a coil spring or rubber, or have any other structures.

The operation mechanism 54 includes the gripping portion 91 and an operation drive mechanism 93.

The gripping portion 91 grips the treatment tool control portion 41 such that the treatment tool control portion 41 is rotatable about the rotational axis A1 extending in the longitudinal direction L1 of the shaft 32, and movable in the longitudinal direction L1 with respect to the shaft 32. Further, the gripping portion 91 is supported so as to be rotatable (swingable) about a drive shaft 94 supported on the housing 51.

A grip position B1 is a position of the gripping portion 91 in a state in which the instrument 4b is coupled to the grip mechanism 30. A released position B2 is a position of the gripping portion 91 in a state in which the instrument 4b is decoupled from the grip mechanism 30, and is also a position of the gripping portion 91 during the replacement of the instrument 4b. The gripping portion 91 does not grip the treatment tool control portion 41 when the gripping portion 91 is at the released position B2.

The present example configuration will be described based on the state in which the instrument 4b is attached to the grip mechanism 30, unless otherwise described. In other words, the present example configuration will be described based on a state in which the gripping portion 91 grips the treatment tool control portion 41 at the grip position B1, unless otherwise described.

As illustrated in FIG. 7, the gripping portion 91 has an open end in a radial direction R1 of the drive shaft 94. The gripping portion 91 includes, at a portion closer to the opening, a space S (a cylindrical or elongate space S) capable of housing the treatment tool control portion 41. The inner surface of the gripping portion 91 (the inner surface defining the space S in the gripping portion 91) closer to the opening extends generally straight from a side closer to the drive shaft 94 toward the open end of the space S (i.e., along the radial direction of the drive shaft 94). This structure allows the treatment tool control portion 41 to be displaced, in the gripping portion 91, with respect to the gripping portion 91 in the longitudinal axis direction L2 of the space S along the radial direction R1 of the drive shaft 94. In other words, the gripping portion 91 grips the treatment tool control portion 41 such that the treatment tool control portion 40 can be relatively displaced in the longitudinal axis direction L2 of the space S of the gripping portion 91 along the radial direction R1 of the drive shaft 94.

The bottom portion of the gripping portion 91 closer to the opening is provided with an elongate hole 101 which communicates the space S of the gripping portion 91 and the outside of the gripping portion 91 and through which the treatment tool control portion 41 passes. The elongate hole 101 extends in the longitudinal axis direction L2 of the space S along the radial direction R1 of the drive shaft 94. It is preferable that a portion where the treatment tool control portion 41 having a spherical shape is inserted is tapered. This structure allows the gripping portion 91 to grip the spherical treatment tool control portion 41 in a stable posture.

In the present example configuration, an adopter 103 is provided for filling the gap between the treatment tool control portion 41 and the gripping portion 91. The adopter 103 is made of an elastic member, such as rubber. As the adopter, the elastic member may be attached to an inner surface of the gripping portion 91. The treatment tool control portion 41 may be in direct contact with the gripping portion 91 without the adopter 103.

Further, the gripping portion 91 is configured to receive a biasing member 108. The biasing member 108 biases the gripping portion 91 in the direction from the grip position B1 to the released position B2. The biasing member 108 in the present example configuration is a coil spring. However, the biasing member 108 may be comprised of another elastic (e.g., rubber) member.

The biasing member 108 is in a free state (a state in which no external force is given) when the gripping portion 91 is at the released position B2 (see FIG. 11). In the free state, no biasing force is applied to the gripping portion 91. On the other hand, the biasing member 108 is compressed by the displacement of the gripping portion 91 from the released position B2 to the grip position B1. The biasing member 108 therefore gives elastic resilience, which is a biasing force, to the gripping portion 91. The drive shaft 94 and the gripping portion 91 having the above configuration are driven to rotate by the operation drive mechanism 93.

The operation drive mechanism 93 includes a second actuator 112 which transmits a driving force to the gripping portion 91 and the drive shaft 94 via a speed reducer mechanism, such as a gear mechanism, and a second encoder 113.

The second actuator 112 is an electric motor in this example configuration, but is not limited to a specific configuration as long as the second actuator 112 can rotatably drive the drive shaft 94.

The second encoder 113 serves as a position detector, and is attached to the second actuator 112. The encoder as the position detector may be replaced with a resolver or a potentiometer.

In this configuration, the drive shaft 94 is rotated by the rotation of the output shaft of the second actuator 112. The gripping portion 91 is rotated with the rotation of the drive shaft 94.

The first actuator 83 and the second actuator 112 are electrically connected with the controller 6 (see FIG. 1). A treatment tool operation instruction is input to the controller 6 based on a movement instruction input to the operating apparatus 2. The treatment tool operation instruction indicates a position of the treatment tool 34 of the instrument 4b around the rotational axis A1 and a degree of opening/closing of the treatment tool 34. The controller 6 servo-controls the first and second actuators 83, 112, based on the treatment tool operation instruction and the rotational angle detected by the first and second encoders 84, 113. In this manner, the controller 6 controls the treatment tool 34 such that the treatment tool 34 reaches the position and achieves the degree of opening/closing which are indicated by the treatment tool operation instruction.

Now, how the instrument 4b is attached to, or detached from, the grip mechanism 30 will be described.

With reference to FIGS. 6, 10 and 11, the gripping portion 91 is held at the released position B2 by the biasing member 108 while the instrument 4b is not attached to the grip mechanism 30.

When the instrument 4b passes through the cover 56 and is inserted in the grip mechanism 30 from the distal end of the inner cover 61 in a straight manner from this state, the treatment tool control portion 41 of the instrument 4b is housed in the gripping portion 91 from the open end. Further insertion of the instrument 4b in the longitudinal direction L1 causes the treatment tool control portion 41 to displace the gripping portion 91 toward the grip position B1 against the biasing force of the biasing member 108.

Further, the shaft 32 of the instrument 4b is frictionally coupled to the tool support 57 by being inserted in the through hole 59.

The shaft 32 of the instrument 4b is coupled to the retaining mechanism 80, as well, when the gripping portion 91 reaches the grip position B1, which contributes to more reliable prevention of slipping-off from the housing 51. Further, the treatment tool control portion 41 can be operated by the gripping portion 91 gripping the treatment tool control portion 41.

On the other hand, to pull the instrument 4b out of the grip mechanism 30, the instrument 4b is pulled such that the instrument 4b comes off from the grip mechanism 30 along the longitudinal direction L1. Pulling the shaft 32 with a force greater than a specific force causes the retaining mechanism 80 to release the shaft 32, and the shaft 32 is removed against the friction with the tool support 57. The above is merely a basic configuration. The grip mechanism 30 can grip and operate instruments in different types and sizes, and may also be configured as follows.

The tool support 57 may be configured as a member in which a portion contacting with the shaft is made of an elastic material, such as rubber, to correspond to shafts having a certain degree of variation in sizes. Alternatively, the tool support unit 52 may be replaced so as to correspond to instruments whose shafts have different diameter sizes. In this case, the inner cover 61 with a hole 63 having a size allowing the shaft 32 to pass therethrough may be used to correspond to the size of the instrument 4b, or the tool support unit 52 may be configured by combining the bearings 69, 77 and the gear 75, the sizes of which appropriately correspond to the size of the instrument 4b, and the tool support 57, the shape of which appropriately corresponds to the shape of the instrument 4b. A speed reduction ratio can be changed by changing the size of the gear 75.

The configurations and elements disclosed in the present example may be appropriately changed and/or omitted. For example, the retaining mechanism 80 may be omitted as long as the tool support 57 supports the shaft 32 reliably by a frictional or biasing force. Moreover, how to bias the gripping portion 91 and/or the presence or absence of the speed reducer may also be changed appropriately.

Figure 12A:
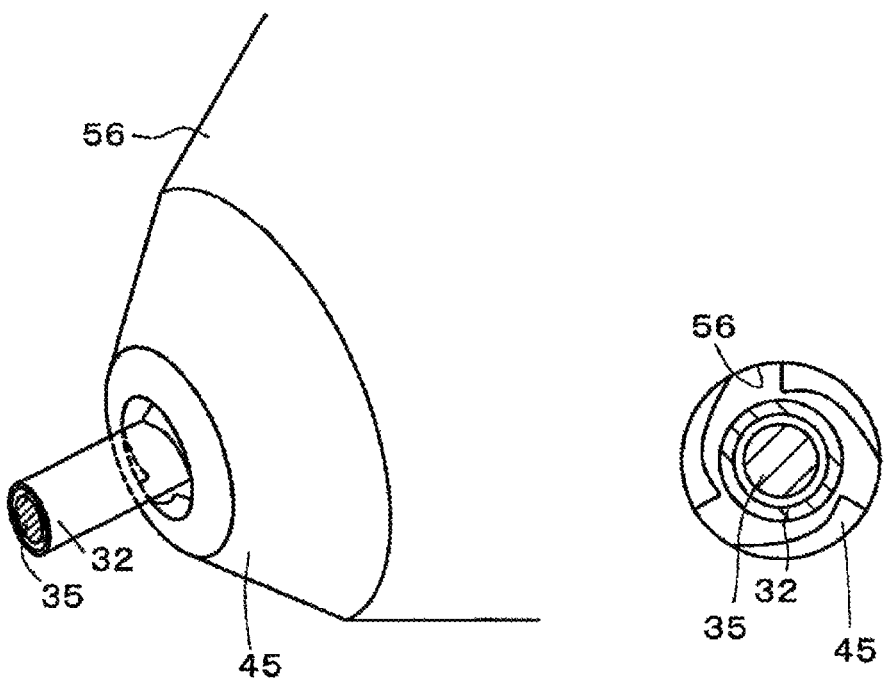
FIG. 12A illustrates a perspective view and a bottom view of an opening adjusting mechanism, with its opening widened and a large-diameter instrument attached to the opening. Part of the opening adjusting mechanism is shown as a cross-section.
Figure 12B:
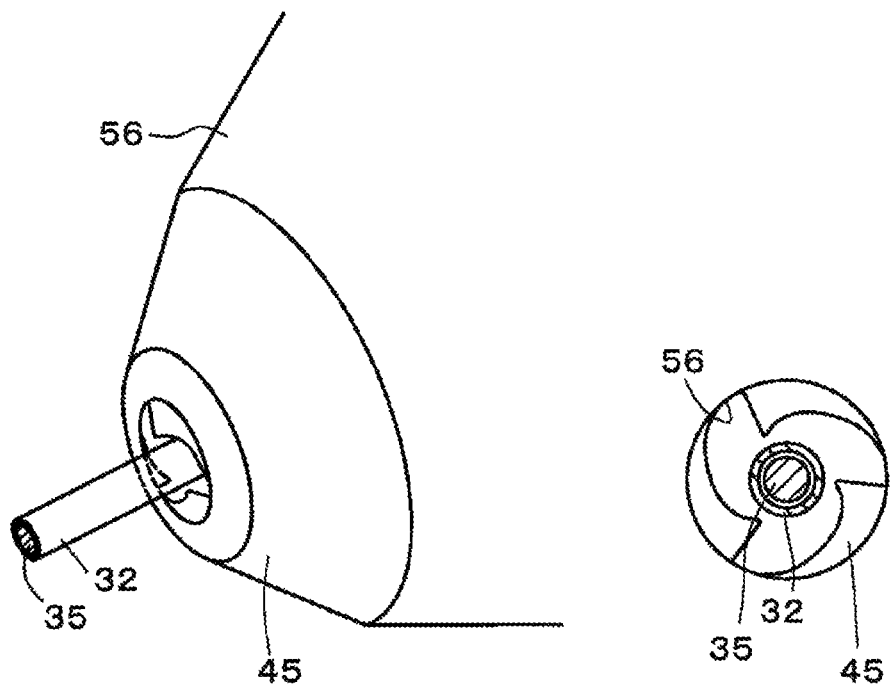
FIG. 12B illustrates a perspective view and a bottom view of the opening adjusting mechanism, with its opening narrowed and a small-diameter instrument attached to the opening. Part of the opening adjusting mechanism is shown as a cross-section.

The diameter size (i.e., the inside diameter) of the opening of the cylindrical portion at the distal end of the cover 56 through which the shaft 32 of the instrument 4b passes may be configured as being adjustable. For example, an opening adjusting mechanism 45 illustrated in FIGS. 12A and 12B may be provided at the distal end of the cover 56. The opening adjusting mechanism 45 is configured to change a degree of extension of a plurality of claws by turning a sleeve provided at the distal end of the opening adjusting mechanism 45.

Alternatively, the cylindrical portion at the distal end of the cover 56, through which the shaft 32 of the instrument 4b passes, may be configured as being detachable from the other part of the cover 56, and multiple types of cylindrical portions having different diameters may be prepared. Alternatively, multiple types of covers 56 may be prepared which include, at the distal ends thereof, cylindrical portions having different diameters (through which the shaft 32 of the instrument 4b passes) so that a cover 56 suitable for the size (i.e., the diameter) of the instrument to be attached may be attached to the housing body 55. Moreover, although the cover 56 provides better protection and appearance, these advantages may be ignored and the cover 56 may be omitted. With the omission of the cover 56, the ball plunger 72 may also be omitted.

Depending on the type of the instrument 4b attached, a motion range (i.e., a stroke) of the treatment tool control portion 41 with respect to the shaft 32 varies. This stroke may be measured by the second encoder 113 by driving the second actuator 112 temporarily in a state in which the treatment tool control portion 41 is attached to the gripping portion 91, and a motion rate (i.e., how much the actuator 112 is driven with respect to an amount of operation of the operation input section 5) may be determined based on the measurement result.

In this manner, according to the present example configuration, the gripping portion 91 grips the treatment tool control portion 41 such that the treatment tool control portion 41 is rotatable about the rotational axis A1 extending in the longitudinal direction L1 of the shaft 32, and movable in the longitudinal direction L1 with respect to the shaft 32. This configuration allows a robot to grip an instrument 4b in such a manner that allows a treatment tool to be rotated and opened/closed, even if the instrument 4b is a general tool used, for example, in surgery performed by a human, and allows the operator to remote control the instrument 4b.

In the present example configuration, an elongate hole 101 may be provided at the bottom of the opening of the gripping portion 91 as an example configuration of the gripping portion 91.

In the present example configuration, the treatment tool 34 and the treatment tool control portion 41 are coupled to each other with the rod 35 which passes through the inside of the shaft 32. This configuration allows reliable transmission of the operation to the treatment tool 34.

In the present example configuration, a proximal end portion of the rod 35, which has a smaller diameter than a middle portion of the rod 35, passes through the elongate hole 101 formed in the bottom of the opening of the gripping portion 91 in a state in which the treatment tool control portion 41 is gripped by the gripping portion 91.

In the present example configuration, the tool support 57 supports the shaft 32 such that the shaft 32 is rotatable about the axis A1 extending in the longitudinal direction L1 in the state in which the treatment tool control portion 41 is gripped by the gripping portion 91. According to this configuration, the tool support 57 has the function of rotatably supporting the shaft 32, and the gripping portion 91 has the function of operating the treatment tool control portion 41.

In the present example configuration, the gripping portion 91 is supported on the drive shaft 94 so as to be rotatable about the drive shaft 94. This configuration allows the treatment tool control portion 41 to be attached to, or detached from, the gripping portion 91 by simply rotating the gripping portion 91 about the drive shaft 94.

In the present example configuration, the gripping portion 91 reaches the released position B2 from the grip position B1 by being rotated about the drive shaft 94 such that the opening of the gripping portion 91 faces the distal end of the shaft 32. According to this configuration, the instrument 4b can be removed from the gripping portion 91 of the grip mechanism 30 by pulling the instrument 4b. The instrument 4b can be attached to, or detached from, the grip mechanism 30 by this simple movement of the instrument 4b with respect to the grip mechanism 30.

In the present example configuration, the biasing member 108 is provided which biases the gripping portion 91 from the grip position B1 toward the released position B2. This configuration allows the gripping portion 91 to be positioned at the released position B2 while the instrument 4b is not attached to the grip mechanism 30. In this configuration, the treatment tool control portion 41 of the instrument 4b is pushed into the grip mechanism 30, and this pushing force of the treatment tool control portion 41 is transmitted to the gripping portion 91, causing the gripping portion 91 to be displaced from the released position B2 to the grip position B1. In this manner, the treatment tool control portion 41 can be attached to the grip mechanism 30 by simply pushing the instrument 4b into the grip mechanism 30.

In the present example configuration, the adopter 103 fills the gap between the treatment tool control portion 41 and the gripping portion 91. This configuration may reduce noise generated by a gap between the gripping portion 91 and the treatment tool control portion 41. Further, this configuration may adjust friction between the gripping portion 91 and the treatment tool control portion 41 during operation.

In the present example configuration, the retaining mechanism 80 is decoupled from the shaft 32 when a force greater than or equal to a specific value acts between the retaining mechanism 80 and the shaft 32 in the longitudinal direction L1. In this configuration, the instrument 4b may be gripped more reliably, and it is possible to prevent the instrument 4b from slipping from the grip mechanism 30.

In the present example configuration, the shaft 32 is rotated about the rotational axis A1 by the first actuator 83.

In the present example configuration, the housing body 55 is provided with the cover 56. Thus, the shaft 32 may be protected more reliably.

In the present example configuration, the gripping portion 91 is driven by the second actuator 112 of the operation drive mechanism 93, thereby displacing the treatment tool control portion 41 in the longitudinal direction L1.

[Second Example Configuration]

Now, a second example configuration of one or more embodiments will be described. In the following description, different configurations from those of the first example configuration will be mainly described. Also, the same reference characters will be used to designate similar configurations to those of the first example configuration, and detail explanations of the similar configurations may be omitted herein.

Figure 13:
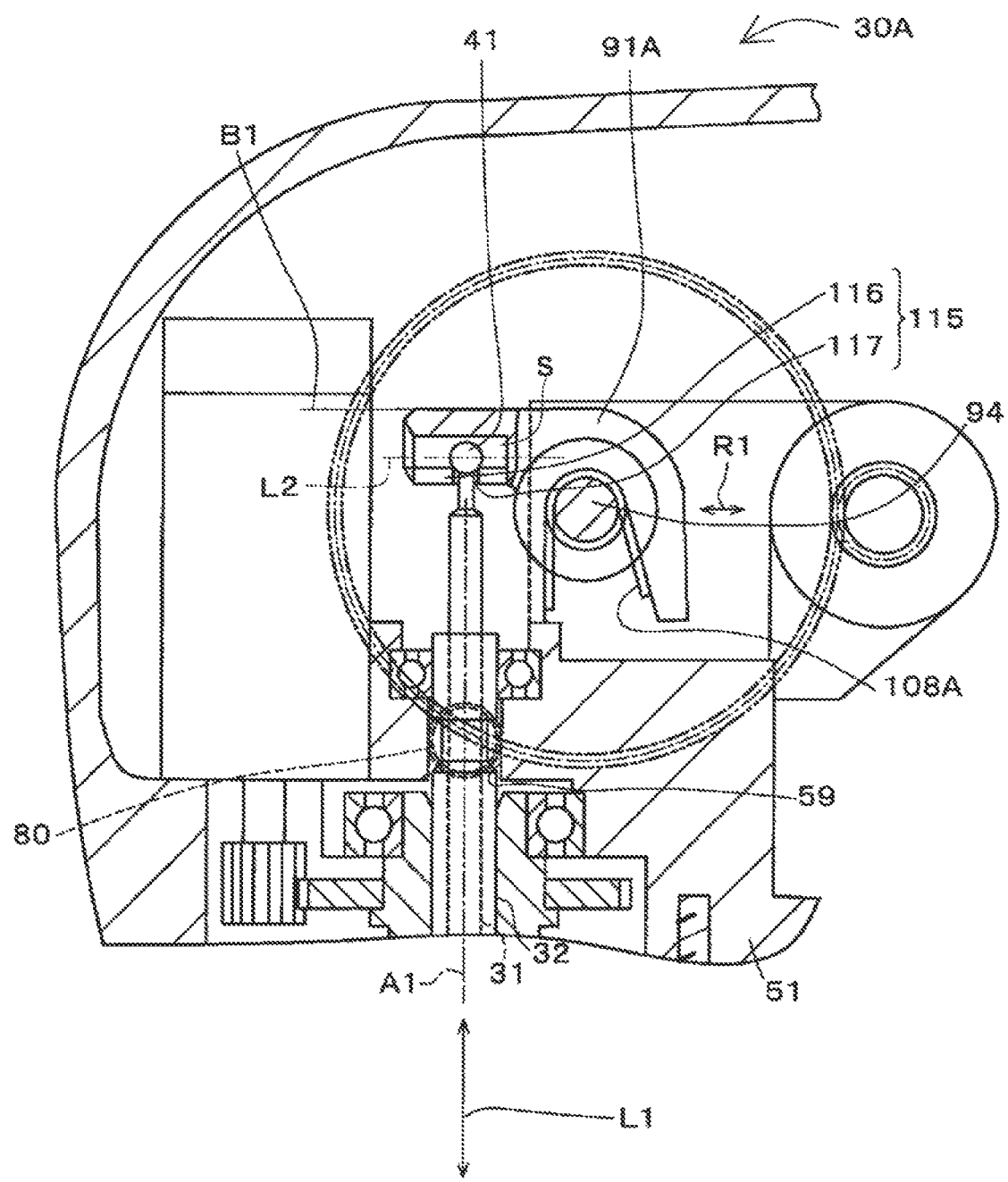
FIG. 13 is a diagram illustrating a cross-sectional view of a main part of a grip mechanism according to a second example configuration of one or more embodiments, as viewed from the side.
Figure 14:
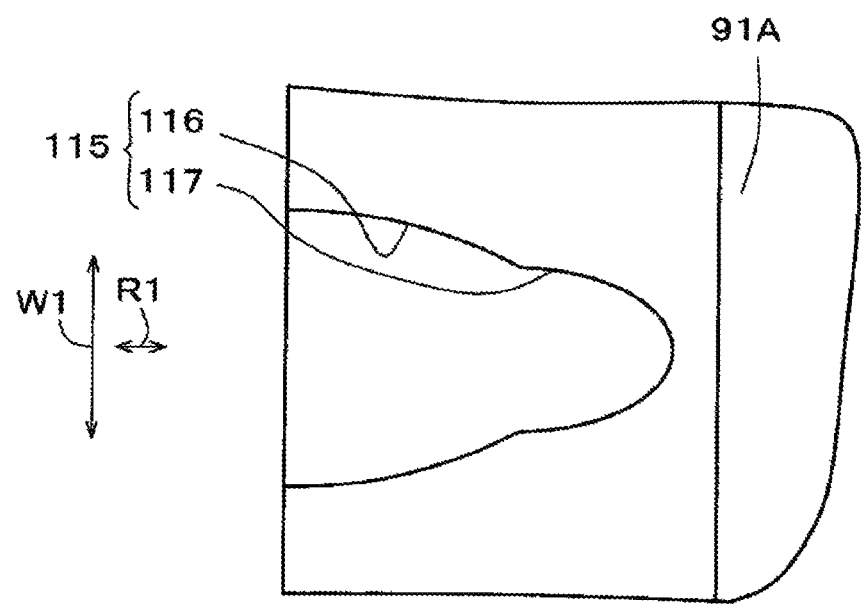
FIG. 14 is a diagram illustrating a bottom view of the gripping portion of the grip mechanism near the open end of the gripping portion.
Figure 15A:
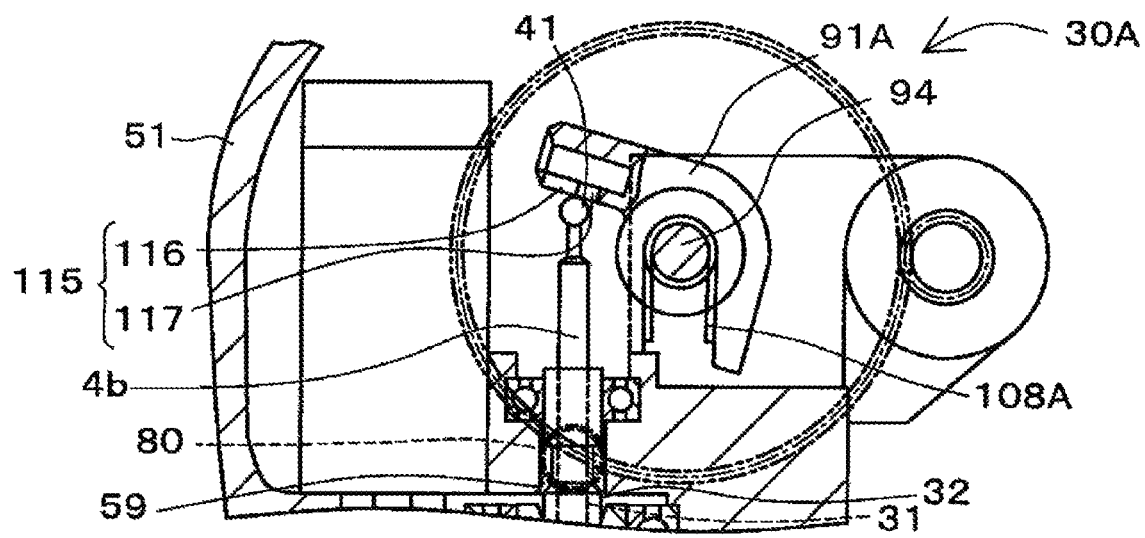
FIG. 15A shows how an instrument is attached and detached, and illustrates a state in which the gripping portion is pushed up.
Figure 15B:
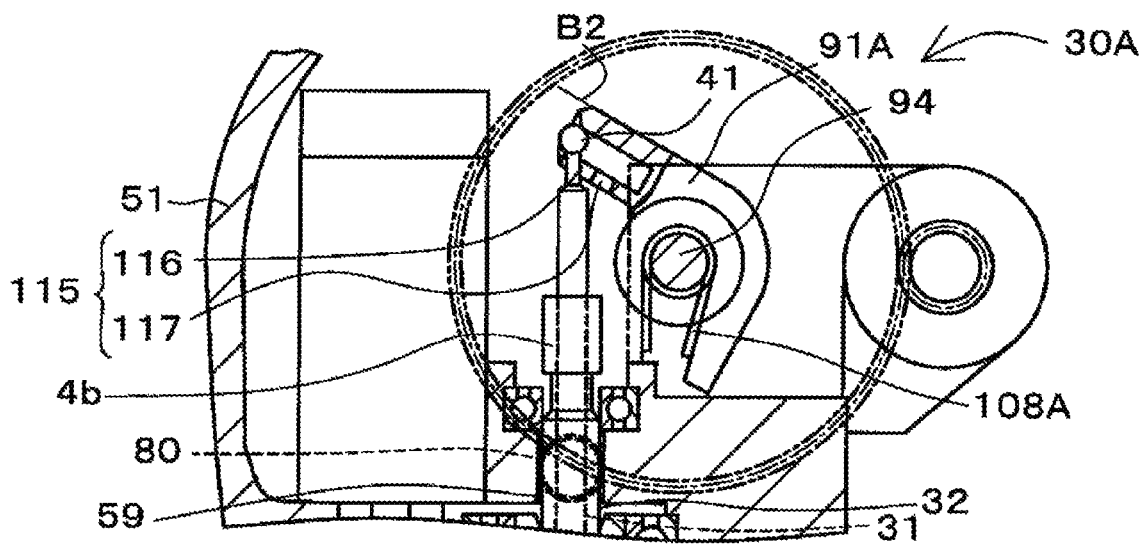
FIG. 15B shows how the instrument is attached and detached, and illustrates a state in which the treatment tool control portion has entered the gripping portion.
Figure 15C:
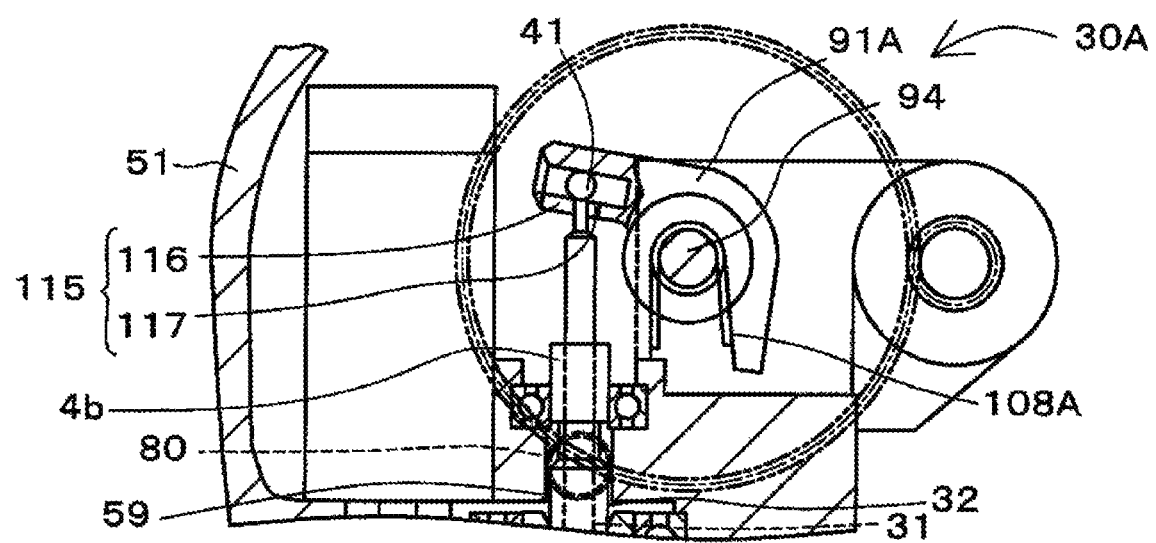
FIG. 15C shows how the instrument is attached and detached, and illustrates a state in which the treatment tool control portion has entered the gripping portion.

FIG. 13 is a diagram illustrating a cross-sectional view of a main part of a grip mechanism 30A according to the second example configuration of one or more embodiments, as viewed from the side. FIG. 14 is a diagram illustrating a bottom view of the gripping portion 91A of the grip mechanism 30A near the open end of the gripping portion 91A. FIGS. 15A-15C illustrate how the instrument 4b is attached and detached. FIG. 15A illustrates a state in which the gripping portion 91A is pushed up. FIG. 15B illustrates a state in which the treatment tool control portion 41 enters the gripping portion 91A. FIG. 15C illustrates a state in which the treatment tool control portion 41 enters the gripping portion 91A.

With reference to FIGS. 13 and 14, the grip mechanism 30A differs from the grip mechanism 30 of the first example configuration in the configurations of the gripping portion 91A and a biasing member 108A. The gripping portion 91A is configured to reach the released position B2 from the grip position B1 by being rotated about the drive shaft 94 in a direction in which the open end of the gripping portion 91A moves away from the distal end of the shaft 32 (i.e., in a direction from the distal end toward the proximal end of the shaft 32 along the longitudinal direction L1).

The gripping portion 91A grips the treatment tool control portion 41 when the gripping portion 91A is at the grip position B1. The released position B2 is where the gripping portion 91A is positioned during replacement of the instrument 4b. The gripping portion 91A does not grip the treatment tool control portion 41 when the gripping portion 91 is at the released position B2.

A notch 115 is formed at a bottom portion of the gripping portion 91A closer to the opening. The notch 115 includes a narrower portion 117 and a wider portion 116. The wider portion 116 is arranged on the open end side along the radial direction R1. The length of the wider portion 116 in the width direction W1 is greater than the diameter of the treatment tool control portion 41. On the other hand, the length of the narrower portion 117 in the width direction W1 is smaller than the diameter of the treatment tool control portion 41, and is greater than the diameter of a smaller diameter portion of the rod 35 on the proximal end thereof (i.e., the diameter of a portion of the rod 35 which passes through the notch 115).

Now, how the instrument 4b is attached or detached in the present example configuration will be described.

With reference to FIGS. 13, 14 and 15A-15C, the gripping portion 91A is held at the grip position B1 (see FIG. 15A) by the biasing member 108A while the instrument 4b is not attached to the grip mechanism 30A.

When the instrument 4b is inserted in the grip mechanism 30A in a straight manner from this state, the treatment tool control portion 41 of the instrument 4b pushes the bottom portion of the gripping portion 91A closer to the opening (see FIG. 15A). The gripping portion 91A is accordingly rotated about the drive shaft 94, and is displaced toward the released position B2. Further upward movement of the open end of the gripping portion 91A leads the treatment tool control portion 41 to the wider portion 116 of the notch 115 at the bottom portion of the gripping portion 91A closer to the opening. As a result, the spherical treatment tool control portion 41 is fitted in the gripping portion 91A (FIG. 15B).

Pulling down the shaft 32 in this state causes the smaller diameter portion of the rod 35 to be inserted in the narrower portion 117 of the notch 115 at the bottom portion of the gripping portion 91A closer to the opening (see FIG. 15C). As a result, the gripping portion 91A reaches the grip position B1 (see FIG. 13) while the treatment tool control portion 41 is gripped by the gripping portion 91A.

The shaft 32 of the instrument 4b is coupled to the retaining mechanism 80 when the gripping portion 91A reaches the grip position B1, which may prevent the shaft 32 from slipping off from the housing 51.

On the other hand, to pull the instrument 4b out of the grip mechanism 30A, the instrument 4b is pushed deep into the housing 51 such that the gripping portion 91A is rotated about the drive shaft 94 and is displaced toward the released position B2 (see FIG. 15C). Further upward movement of the gripping portion 91A leads the treatment tool control portion 41 to the wider portion 116 of the notch 115 at the bottom portion of the gripping portion 91A closer to the opening (see FIG. 15B). Subsequently, the instrument 4b is pulled out of the grip mechanism 30A in a quick manner. In this manner, the treatment tool control portion 41 is removed from the gripping portion 91A by way of the wider portion 116 of the notch 115 (see FIG. 15A). At this moment, the second actuator 112 is preferably driven to hold the gripping portion 91A at the released position B2.

In this manner, according to the present second example configuration, the gripping portion 91A grips the treatment tool control portion 41 such that the treatment tool control portion 41 is rotatable about the rotational axis A1, and movable in the longitudinal direction L1 with respect to the shaft 32. This configuration, too, allows a robot to grip an instrument 4b in such a manner that allows a treatment tool to be rotated and opened/closed, even if the instrument 4b is a general tool used, for example, in surgery performed by a human, and allows the operator to remote control the instrument 4b.

[Third Example Configuration]

Now, a third example configuration of one or more embodiments will be described. In the following description, different configurations from those of the first and second example configurations will be mainly described. Also, the same reference characters will be used to designate similar configurations to those of the first and second example configurations, and detail explanations of the similar configurations may be omitted herein.

Figure 16:
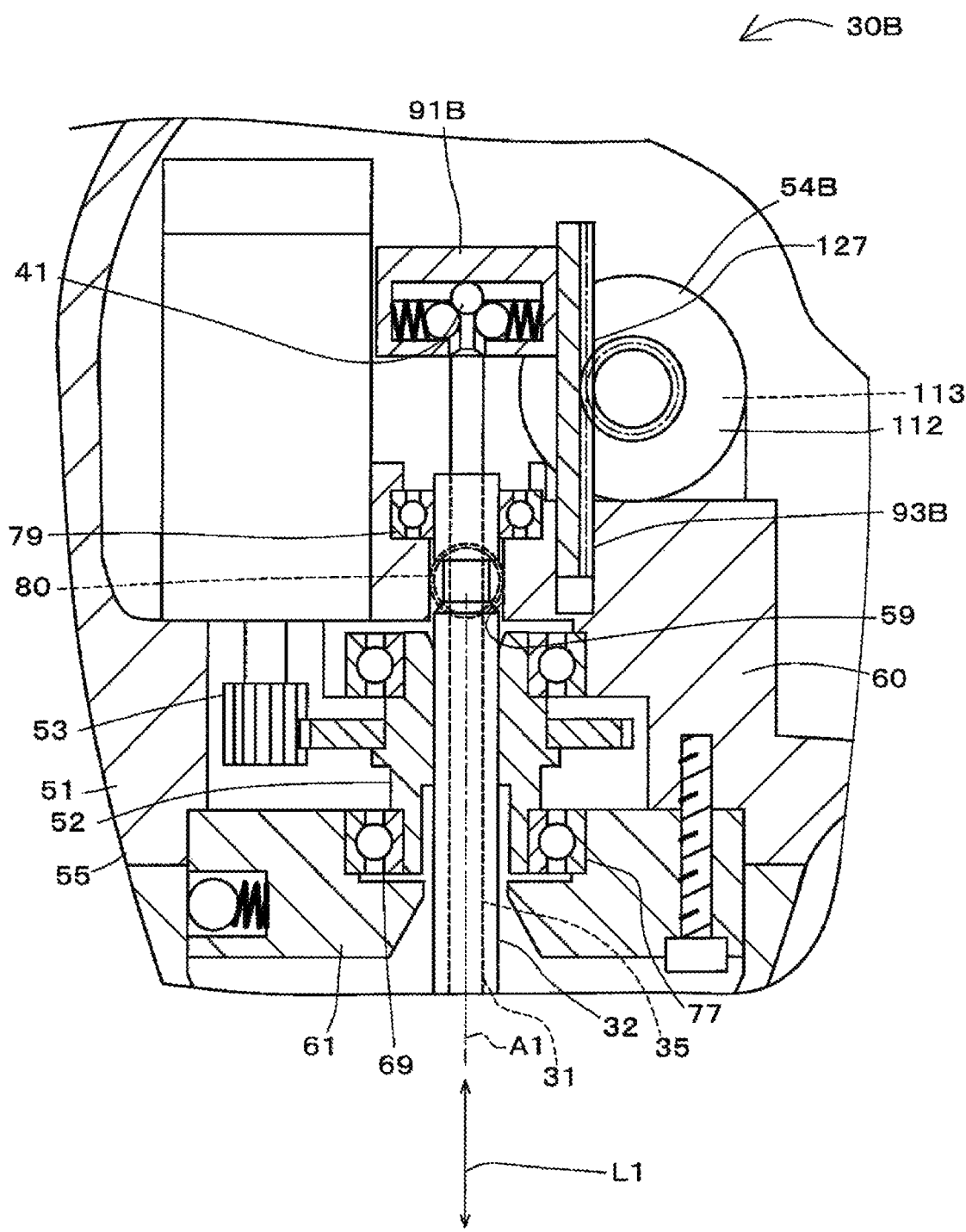
FIG. 16 is a diagram illustrating a cross-sectional view of a main part of a grip mechanism according to a third example configuration of one or more embodiments, as viewed from the side.
Figure 17:
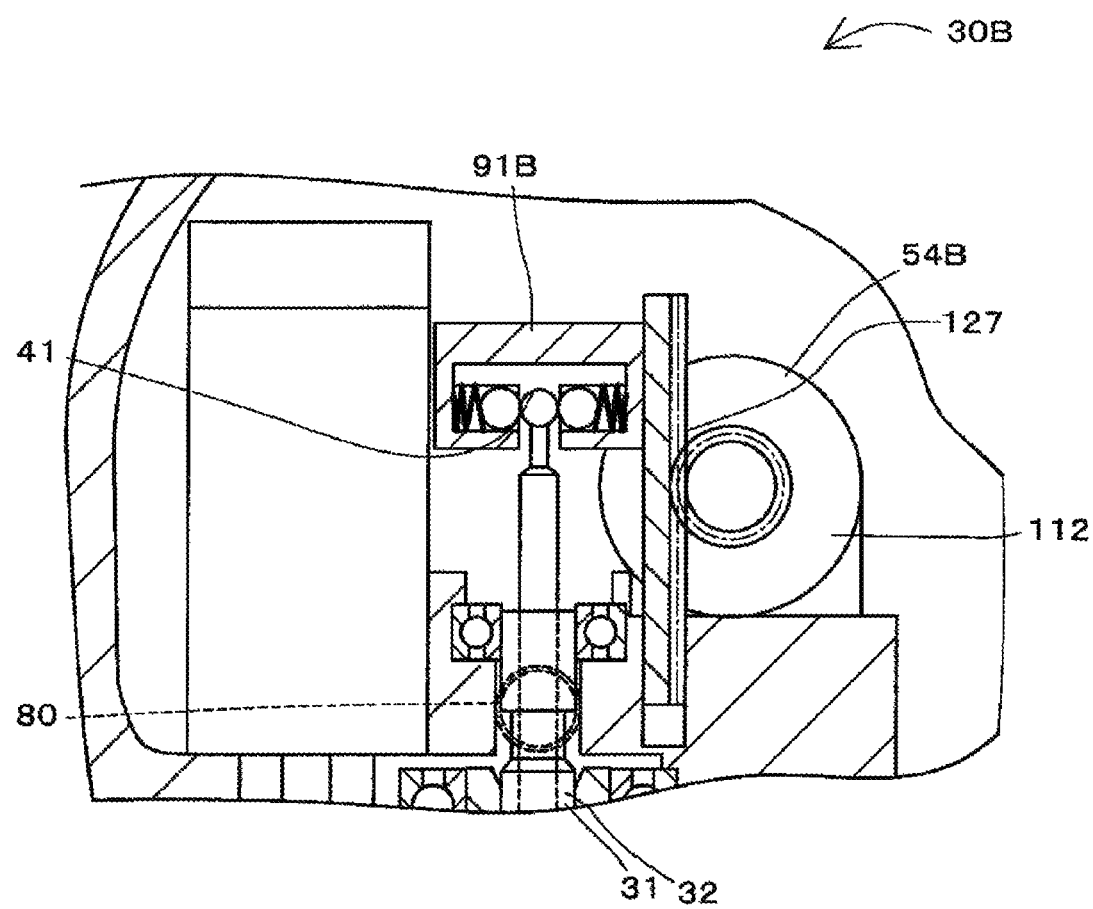
FIG. 17 is a diagram illustrating a cross-sectional view of the main part of the grip mechanism, as viewed from the side, to show how the instrument is attached and detached.

FIG. 16 is a diagram illustrating a cross-sectional view of a main part of a grip mechanism 30B according to the third example configuration of one or more embodiments, as viewed from the side. FIG. 17 is a diagram illustrating a cross-sectional view of a main part of the grip mechanism 30B, as viewed from the side, to show how the instrument 4b is attached and detached.

With reference to FIGS. 16 and 17, the third example configuration utilizes an operation mechanism 54B instead of the operation mechanisms 54 of the first and second example configurations.

The operation mechanism 54B supports a gripping portion 91B and an operation drive mechanism 93B which supports and drive the gripping portion 91B.

The gripping portion 91B is a member which grips the treatment tool control portion 41 such that the treatment tool control portion 41 is rotatable about the rotational axis A1 extending in the longitudinal direction L1 of the shaft 32, and movable in the longitudinal direction L1 with respect to the shaft 32. The gripping portion 91B is coupled to the treatment tool control portion 41 so as to be relatively rotatable about the rotational axis A1, and integrally displaceable in the longitudinal direction L1, with respect to the treatment tool control portion 41.

The gripping portion 91B includes a pair of ball plungers housed in a case. Each ball plunger includes an elastic member, such as a coil spring or rubber, and a ball pressed toward the treatment tool control portion 41 by the elastic member.

Points of the pair of ball plungers which come in contact with the treatment tool control portion 41 can be adjusted according to the shape of the treatment tool control portion 41 of the instrument 4b. It is therefore possible to attach treatment tool control portions 41 in different types and diameters. The gripping portion 91B is not limited to the ball plunger. The gripping portion 91B may have only the elastic member, such as a coil spring or rubber, or have any other structures.

The operation drive mechanism 93B includes a motion conversion mechanism 127, a second actuator 112, and a second encoder 113.

The motion conversion mechanism 127 is provided to convert from a rotational motion to a linear motion, and vice versa. In the third example configuration, the motion conversion mechanism 127 is a rack and pinion mechanism, which includes a rack attached to the gripping portion 91B and slidably supported on the housing body 55, and a pinion coupled to an output shaft of the second actuator 112 and meshing with the rack. Rotation of the output shaft of the second actuator 112 is converted to a linear motion of the gripping portion 91B by the motion conversion mechanism 127. Thus, the treatment tool control portion 41 is displaced in the longitudinal direction L1, thereby operating the treatment tool 34.

In this manner, according to the present third example configuration, the gripping portion 91B grips the treatment tool control portion 41 such that the treatment tool control portion 41 is rotatable about the rotational axis A1, and movable in the longitudinal direction L1 with respect to the shaft 32. This configuration allows a robot to grip an instrument 4b in such a manner that allows a treatment tool to be rotated and opened/closed, even if the instrument 4b is a general tool used, for example, in surgery performed by a human, and allows the operator to remote control the robot.

Non-limiting example configurations of one or more embodiments have been described in the above description, but various modifications are possible within the scope of claims. For example, one or more embodiments may also be modified as follows.

Figure 18:
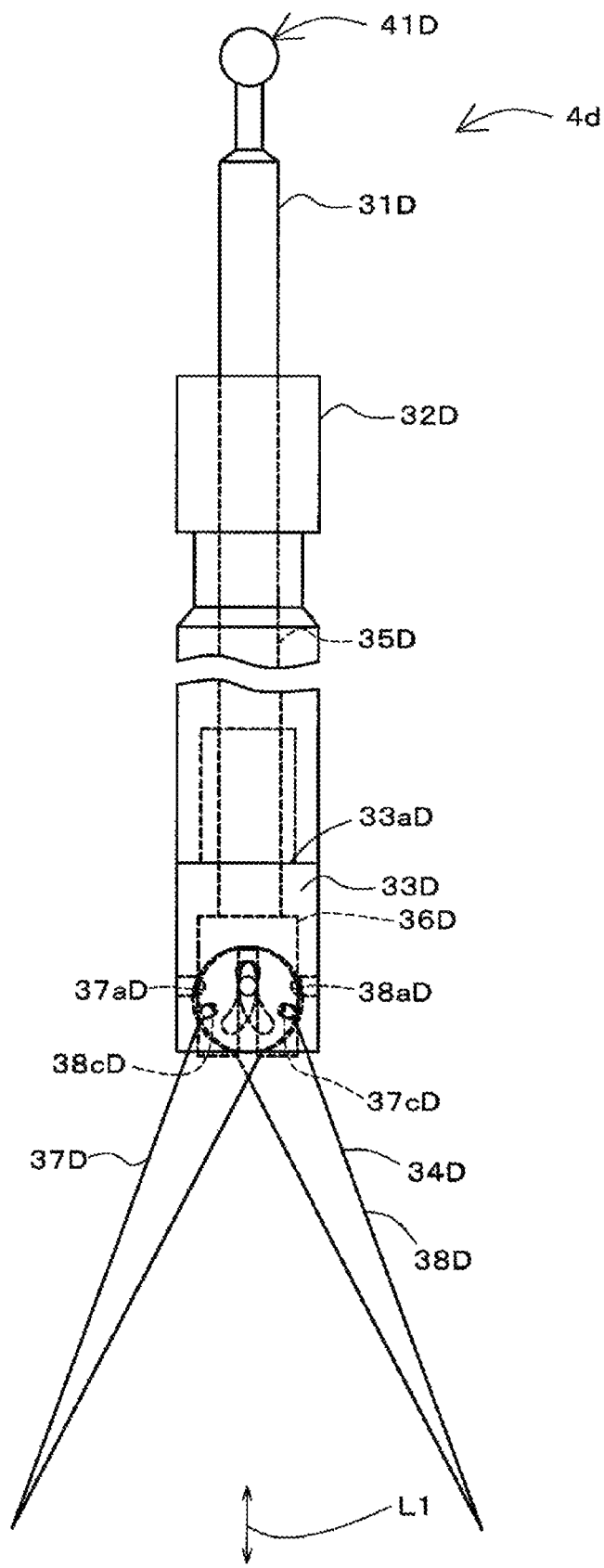
FIG. 18 is a diagram illustrating a side view of an example configuration of a pair of scissors as another instrument.

(1) In the above example configurations, an example in which the instrument 4b is a grasper has been described. However, as mentioned earlier, the grip mechanism of one or more embodiments is configured such that instruments in different types and diameters can be attached thereto. An instrument 4d illustrated in FIG. 18 may also be used as another example of the instruments.

Main differences between the instrument 4d and the instrument 4b are the configuration of the treatment tool 34D and the diameters of the shaft 32D and the rod 35D.

In this example configuration, the instrument 4d is a pair of scissors, and is typically used to make an incision in a body tissue of the treatment target P. The instrument 4d may be a monopolar tool.

The instrument 4d is comprised of an insert 31D, a shaft 32D, an insert end portion 33D, and a treatment tool 34D. When used, the insert 31D and the shaft 32D are coupled to each other, with the insert 31D being inserted in the shaft 32D.

The outside diameter of the shaft 32D is greater than the outside diameter of the shaft 32 of the instrument 4b. The outside diameter of the rod 35D is greater than the outside diameter of the rod 35 of the instrument 4b. The outside diameter of the insert end portion 33D is greater than the outside diameter of the insert end portion 33 of the instrument 4b.

The treatment tool 34D includes a pair of elongate blades 37D, 38D in this example configuration. The blade 37D is provided, at its proximal end, with a fulcrum point portion 37aD coupled to a bearing portion provided at the insert end portion 33D, and a load point portion 37cD coupled to a drive shaft provided at a linkage portion 36D. The displacement of the insert 31D (the linkage portion 36D) in the longitudinal direction L1 causes the blade 37D to swing about the fulcrum point portion 37aD.

The blade 38D has a configuration similar to that of the blade 37D, and moves in conjunction with the blade 37D. The blade 38D is provided, at its proximal end, with a fulcrum point portion 38aD coupled to the bearing portion provided at the insert end portion 33D, and a load point portion 38cD coupled to the drive shaft provided at the linkage portion 36D. The displacement of the insert 31D (the linkage portion 36D) in the longitudinal direction L1 causes the blade 38 to swing about the fulcrum point portion 38aD.

In this example configuration, the treatment tool control portion 41D having a spherical shape is gripped by the gripping portion 91, 91A, 91B of the grip mechanism 30, 30A, 30B.

Also in a case in which the instrument 4d is used instead of the instrument 4b, the treatment tool control portion 41D is gripped by the gripping portion 91, 91A, 91B. That is, multiple types of instruments 4b, 4d may be gripped by the grip mechanism 30, 30A, 30B.

Figure 19:
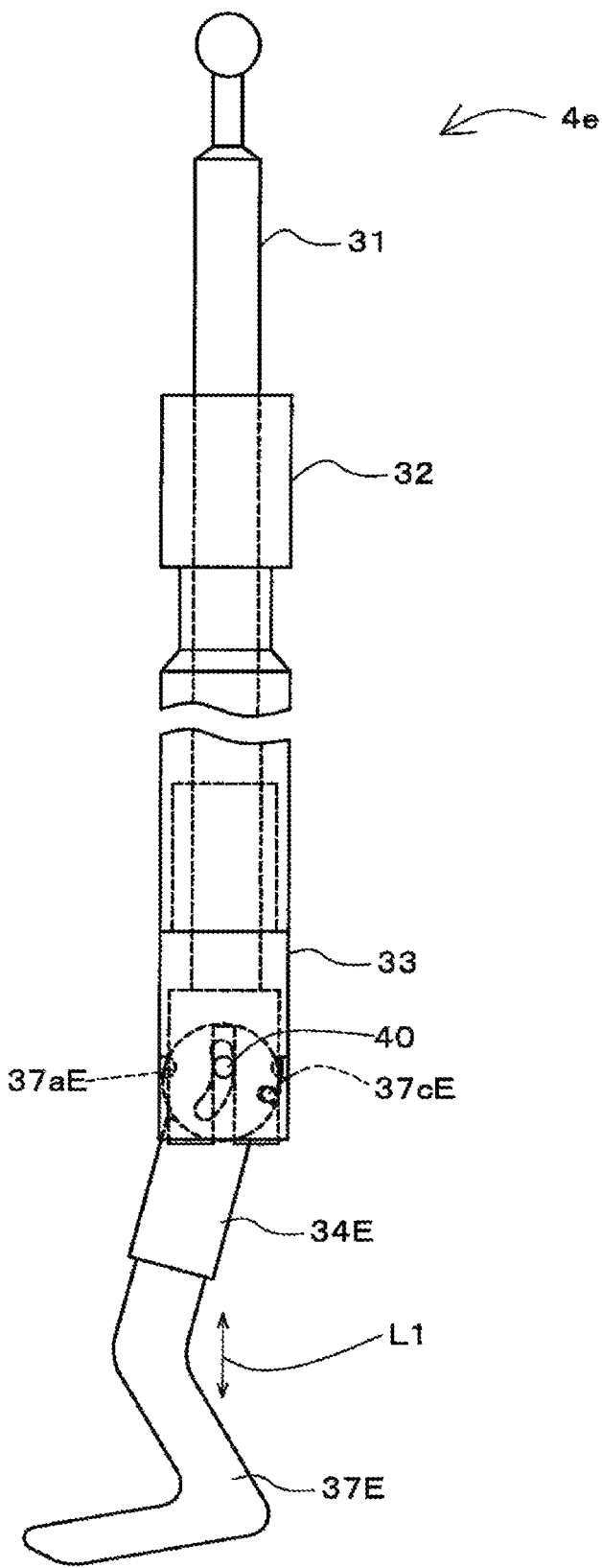
FIG. 19 is a diagram illustrating a side view of an example configuration of a hook as another instrument.

(2) Further, an instrument including a single end effector, such as a hook, may be used instead of the instrument 4b. FIG. 19 is a diagram illustrating a side view of an example instrument 4e including a single end effector. In FIG. 19, part of the instrument 4e is not shown. In this example configuration, the instrument 4e is a hook, and is typically used to pull up part of a body tissue of the treatment target P. The instrument 4e may be a monopolar tool.

A difference between the configurations of the instrument 4e and the instrument 4b is a configuration of a treatment tool 34E. Specifically, the instrument 4e is comprised of the insert 31, the shaft 32, the insert end portion 33, and a treatment tool 34E. When used, the insert 31 and the shaft 32 are coupled to each other, with the insert 31 being inserted in the shaft 32.

The treatment tool 34E includes a single hook 37E in this example configuration. The hook 37E is provided, at its proximal end, with a fulcrum point portion 37aE coupled to a bearing portion provided at the insert end portion 33, and a load point portion 37cE coupled to a drive shaft provided at the linkage portion 36. The displacement of the insert 31 (the linkage portion 36) in the longitudinal direction L1 causes the hook 37E to swing about the fulcrum point portion 37aE.

Figure 20:
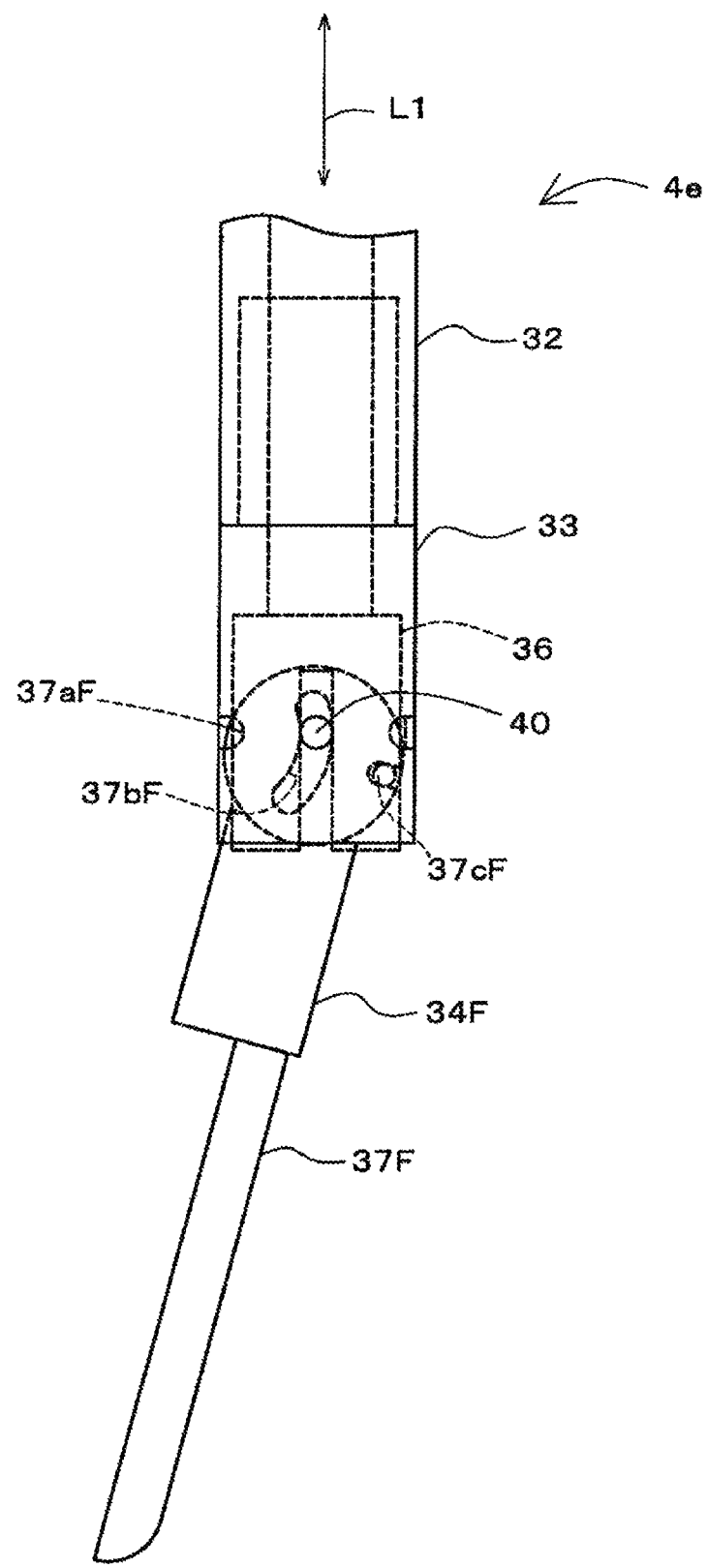
FIG. 20 is a diagram illustrating a side view of an example configuration of a spatula as another instrument.

(3) A spatula 37F may be attached instead of the hook 37E, as illustrated in FIG. 20. The spatula 37F is provided, at is proximal end, with a fulcrum point portion 37aF, an arc-shaped hole 37bF, and a load point portion 37cF. The displacement of the insert 31 (the linkage portion 36) in the longitudinal direction L1 causes the spatula 37F to swing about the fulcrum point portion 37aF.

Figure 21:
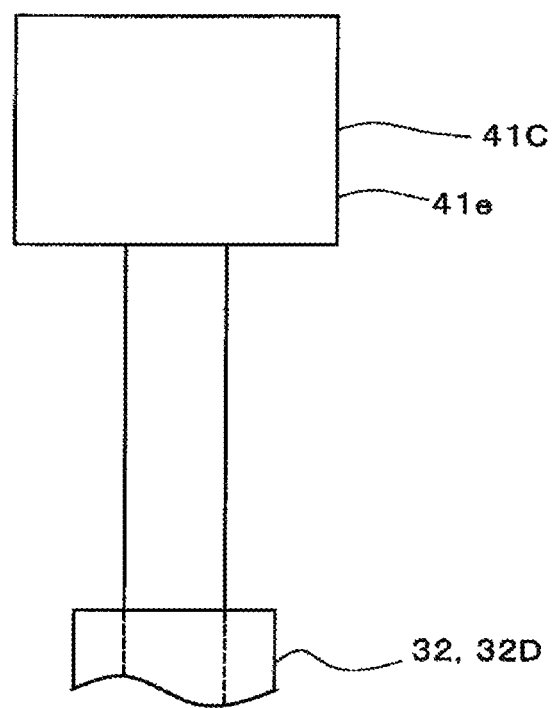
FIG. 21 is a diagram illustrating a main part of an example configuration as another instrument.

(4) The treatment tool control portions 41 of the above-described instruments 4b, 4d and 4e have a spherical shape. However, this is a non-limiting example. For example, as illustrated in FIG. 21, a treatment tool control portion 41C in the form besides a spherical shape may also be used instead of the treatment tool control portion 41. The treatment tool control portion 41C is received in the corresponding gripping portion 91, 91A, 91B. In the example illustrated in FIG. 21, the treatment tool control portion 41C has a cubic shape. Other examples of the shape of the treatment tool control portion 41C may include a polygonal columnar shape, a circular cylindrical shape, and a polyhedral shape. Further, the treatment tool control portion 41C may have other shapes which can be supported rotatably by the gripping portion 91, 91A, 91B.

(5) In the above example configurations, an example in which the rod 35, 35D (i.e., a metal shaft) forms part of the instrument 4b has been described. However, this is a non-limiting example. For example, an instrument in which a treatment tool control portion and a treatment tool are coupled to each other with a flexible wire may be attached to the grip mechanism 30, 30A, 30B.

INDUSTRIAL APPLICABILITY

One or more embodiments disclosed herein may be widely applicable as a medical tool grip mechanism.

What is claimed is:

1. A medical tool grip mechanism which is configured to grip a medical tool including a shaft extending in a longitudinal axis of the shaft, a treatment tool arranged on a side of one end portion of the shaft in the longitudinal axis of the shaft, and a treatment tool control portion which is arranged on a side of the other end portion of the shaft in the longitudinal axis of the shaft and controls the treatment tool, the medical tool grip mechanism comprising:
a gripping portion which is provided at a distal end of a manipulator arm, is rotatably supported by a drive shaft provided orthogonal to the longitudinal axis of the shaft so as to be rotatable between a grip position and a released position with respect to the manipulator arm about the drive shaft and is configured to grip the treatment tool control portion in such a manner that the treatment tool control portion is movable in the longitudinal axis of the shaft when the gripping portion is being rotated about the drive shaft of the gripping portion,
wherein the gripping portion includes a space for gripping the treatment tool control portion in the grip position, the space having a longitudinal axis thereof extending along a radial axis of the drive shaft in the grip position and having first and second ends along the longitudinal axis of the space such that, when the gripping portion is rotated about the drive shaft from the grip position to the released position, the treatment tool control portion in the space is moved toward the first end of the space along the longitudinal axis of the space while the longitudinal axis of the space of the gripping portion is rotated with respect to the longitudinal axis of the shaft, and
the medical tool grip mechanism is configured to couple the treatment tool control portion of the medical tool to the gripping portion at the grip position in such a manner that the treatment tool control portion is located in the space of the gripping portion and thus gripped by the gripping portion and is configured to decouple the treatment tool control portion of the medical tool from the gripping portion at the released position in such a manner that the treatment tool control portion comes out of the space of the gripping portion from a side of the first end of the space of the gripping portion.

2. The medical tool grip mechanism of claim 1, wherein the treatment tool and the treatment tool control portion are coupled to each other with a rod passing through an inside of the shaft.

3. The medical tool grip mechanism of claim 2, wherein the gripping portion includes an elongate hole which communicates the space with an outside of the gripping portion,
a first end portion of the rod on the side of the other end portion of the shaft has a smaller diameter than a middle portion of the rod, and
the first end portion of the rod passes through the elongate hole in a state in which the treatment tool control portion is gripped by the gripping portion.

4. The medical tool grip mechanism of claim 3, wherein the treatment tool control portion has a diameter larger than a diameter of a second end portion of the rod provided on the side of the one end portion of the shaft, wherein the second end portion of the rod is smaller than a diameter of the middle portion of the rod.

5. The medical tool grip mechanism of claim 1, wherein the treatment tool control portion has a spherical shape.

6. The medical tool grip mechanism of claim 1, comprising: a tool support which supports the shaft such that the shaft is rotatable about a rotational axis extending along the longitudinal axis of the shaft in a state in which the treatment tool control portion is gripped by the gripping portion.

7. The medical tool grip mechanism of claim 6, further comprising: an actuator to rotate the shaft about the rotational axis extending in the longitudinal axis of the shaft.

8. The medical tool grip mechanism of claim 1, wherein the first end of the space of the gripping portion opens in the radial axis of the drive shaft, and the gripping portion is configured to move to the released position from the grip position by being rotated about the drive shaft such that the first end of the space of the gripping portion moves toward the one end portion of the shaft.

9. The medical tool grip mechanism of claim 8, further comprising:
a biasing member which biases the gripping portion in a direction from the grip position toward the released position, or in a direction from the released position toward the grip position.

10. The medical tool grip mechanism of claim 1, wherein the first end of the space of the gripping portion opens in the radial axis of the drive shaft, and the gripping portion is configured to move to the grip position from the released position by being rotated about the drive shaft such that the first end of the space of the gripping portion moves away from the one end portion of the shaft.

11. The medical tool grip mechanism of claim 10, further comprising:
a biasing member which biases the gripping portion in a direction from the grip position toward the released position, or in a direction from the released position toward the grip position.

12. The medical tool grip mechanism of claim 1, further comprising:
an adopter which fills a gap between the treatment tool control portion and the gripping portion.

13. The medical tool grip mechanism of claim 1, further comprising: a retaining mechanism including a pair of plungers supporting the shaft of the medical tool and configured to be decoupled from the shaft in response to a force greater than or equal to a specific value acting between the retaining mechanism and the shaft in the longitudinal axis of the shaft.

14. The medical tool grip mechanism of claim 1, further comprising:
a housing which houses the gripping portion, wherein
the housing includes a housing body and a cover attachable to, and detachable from, the housing body and having an opening through which the shaft passes such that a part of the shaft and the treatment tool is exposed to an outside of the housing and the treatment tool control portion is housed in the housing body.

15. The medical tool grip mechanism of claim 14, comprising:
an opening adjustment mechanism which is provided at the opening of the cove and includes a sleeve, such that the sleeve is rotatable with respect to the opening of the cover to adjust a size of the opening provided at the cover.

16. The medical tool grip mechanism of claim 14, comprising:
an inner cover attached to the housing body and having a hole through which the shaft passes, wherein
the hole is chamfered.

17. The medical tool grip mechanism of claim 1, further comprising: an actuator to displace the treatment tool control portion along the longitudinal axis of the shaft by rotating the gripping portion about the drive shaft.

18. The medical tool grip mechanism of claim 1, further comprising: a first electric actuator configured to rotate the shaft about a rotational axis of the shaft extending along the longitudinal axis of the shaft in response to an instruction from a remote control apparatus; and a second electric actuator configured to rotate the drive shaft to rotate the gripping portion about the drive shaft, so as to move the shaft along the longitudinal axis of the shaft in response to an instruction from the remote control apparatus.

19. A method for attaching and detaching a medical tool which includes a shaft extending in a longitudinal axis of the shaft, a treatment tool arranged on a side of one end portion of the shaft in the longitudinal axis of the shaft, a treatment tool control portion which is arranged on a side of the other end portion of the shaft in the longitudinal axis of the shaft and controls the treatment tool, and a gripping portion which is provided at a distal end of a manipulator arm and rotatably provided about a drive shaft orthogonal to the longitudinal axis of the shaft such that the gripping portion is rotatable about the drive shaft between a grip position and a released position with respect to the manipulator arm and is configured to grip the treatment tool control portion in a space formed in the gripping portion, the space of the gripping portion having a longitudinal axis extending along a radial axis of the drive shaft in the grip position, the method comprising:
attaching the medical tool to the gripping portion, by pushing the shaft along the longitudinal axis of the shaft to push the treatment tool control portion into the space of the gripping portion located at the released position, wherein the pushing of the shaft causes the treatment tool control portion to be inserted into the space from a side of a first end of the space of the gripping portion and then to cause the treatment tool control portion in the space to be moved toward a second end of the space of the gripping portion along the longitudinal axis of the space while the gripping portion is rotated about the drive shaft from the released position to the grip position; and
detaching the medical tool from the gripping portion gripping the medical tool by pulling the shaft in the longitudinal axis of the shaft from the gripping portion to rotate the gripping portion about the drive shaft from the grip position to the released position, wherein the pulling of the shaft causes the treatment tool control portion in the space to be moved toward the first end of the space along the longitudinal axis of the space while the longitudinal axis of the space of the gripping portion is rotated with respect to the longitudinal axis of the shaft is and then the treatment tool control portion to come out of the space of the gripping portion at the released position from the side of the first end of the space of the gripping portion.

* * * * *